(12) United States Patent
Chen et al.

(10) Patent No.: US 12,023,678 B2
(45) Date of Patent: Jul. 2, 2024

(54) GENETIC TESTING DEVICE

(71) Applicant: HC BIO-ENGINEERING (CHENGDU) CO., LTD., Chengdu (CN)

(72) Inventors: Jian Chen, Chengdu (CN); Dejiang Zhou, Chengdu (CN); Jie Li, Chengdu (CN)

(73) Assignee: HC BIO-ENGINEERING (CHENGDU) CO., LTD., Chengdu (CN)

( * ) Notice: Subject to any disclaimer, the term of this patent is extended or adjusted under 35 U.S.C. 154(b) by 0 days.

(21) Appl. No.: 18/032,191

(22) PCT Filed: Oct. 18, 2021

(86) PCT No.: PCT/CN2021/124312
§ 371 (c)(1),
(2) Date: Apr. 17, 2023

(87) PCT Pub. No.: WO2022/083528
PCT Pub. Date: Apr. 28, 2022

(65) Prior Publication Data
US 2023/0390778 A1    Dec. 7, 2023

(30) Foreign Application Priority Data

Oct. 19, 2020  (CN) .......................... 202011116049.5

(51) Int. Cl.
| | | |
|---|---|---|
| *B01L 7/00* | (2006.01) |
| *C12Q 1/686* | (2018.01) |
| *G01N 35/02* | (2006.01) |
| *G01N 35/00* | (2006.01) |
| *G01N 35/04* | (2006.01) |

(52) U.S. Cl.
CPC ................ *B01L 7/52* (2013.01); *C12Q 1/686* (2013.01); *G01N 35/02* (2013.01); *B01L 2300/087* (2013.01); *G01N 2035/00306* (2013.01); *G01N 2035/00346* (2013.01); *G01N 2035/0415* (2013.01)

(58) Field of Classification Search
None
See application file for complete search history.

(56) References Cited

FOREIGN PATENT DOCUMENTS

| | | |
|---|---|---|
| CN | 104893951 A | 9/2015 |
| CN | 107760676 A | 3/2018 |
| CN | 107904156 A | 4/2018 |
| CN | 110628608 A | 12/2019 |
| CN | 211057123 U | * 7/2020 |
| CN | 212504894 U | 2/2021 |

* cited by examiner

*Primary Examiner* — P. Kathryn Wright
(74) *Attorney, Agent, or Firm* — Bayramoglu Law Offices LLC

(57) ABSTRACT

A genetic testing device includes a safety cabinet, a gas flow control system, a first treatment module configured to treat an amplification reagent and a polymerase chain reaction (PCR) plate, a second treatment module configured to treat a reagent, a tip, and a gene sample, a sample injection module configured to inject an amplification reagent into a microwell of a PCR plate, a purification treatment module configured to treat a gene sample, an amplification detection module for gene amplification and detection, a heat sealer configured to seal a PCR plate, a material delivery module A, a material delivery module B, and a material delivery module C.

20 Claims, 11 Drawing Sheets

GENETIC TESTING DEVICE

CROSS REFERENCE TO THE RELATED APPLICATIONS

This application is the national phase entry of International Application No. PCT/CN2021/124312, filed on Oct. 18, 2021, which is based upon and claims priority to Chinese Patent Application No. 202011116049.5, filed on Oct. 19, 2020, the entire contents of which are incorporated herein by reference.

TECHNICAL FIELD

The present disclosure relates to the field of genetic testing and in particular to a genetic testing device.

BACKGROUND

Genetic testing refers to the analysis of a base sequence of a specific DNA fragment, namely, an arrangement mode of adenine, thymine, cytosine, and guanine. Genes are basic units of heredity. A DNA or RNA sequence carrying genetic information transfers the genetic information to the next generation through replication, and can guide the synthesis of a protein to express the genetic information thereof, thereby controlling the expression of a trait of an individual organism. Genetic testing is a technique to detect DNA through blood, other bodily fluid, or cells, specifically including: collecting peripheral venous blood or a tissue cell an individual to be tested, amplifying genetic information, and detecting DNA molecular information in the cell of the individual to be tested by a specific device to analyze gene types and gene defects in the DNA molecular information and determine whether corresponding expression functions are normal. In this way, people can know their genetic information, find pathogenesis or predict a risk of developing a disease. Genetic testing can be used to diagnose a disease and can also be used to predict a risk of developing a disease.

The genetic testing devices in the prior art cannot achieve the automation of a whole detection process, resulting in low genetic testing efficiency.

Therefore, it is urgent to develop a genetic testing device to solve the above problems.

SUMMARY

An objective of the present disclosure is to provide a genetic testing device to solve the above problems.

The present disclosure adopts the following technical solutions to achieve the above objective:

A genetic testing device is provided, including: a safety cabinet, where the safety cabinet is divided into an upper part and a lower part that are isolated from each other and the upper part and the lower part each are divided into three mounting chambers that are isolated from one another. The three mounting chambers of the upper part are a first mounting chamber A, a first mounting chamber B, and a first mounting chamber C, and the three mounting chambers of the lower part are a second mounting chamber A, a second mounting chamber B, and a second mounting chamber C. A first switch door assembly A is provided between the first mounting chamber A and the second mounting chamber A, a first switch door assembly B is provided between the first mounting chamber B and the second mounting chamber B, a first switch door assembly C is provided between the first mounting chamber C and the second mounting chamber C, a second switch door assembly A is provided between the second mounting chamber A and the second mounting chamber B, and a second switch door assembly B is provided between the second mounting chamber B and the second mounting chamber C;

a gas flow control system configured to control gas pressure conditions of the first mounting chamber A, the first mounting chamber B, and the first mounting chamber C;

a first treatment module configured to treat an amplification reagent and a polymerase chain reaction (PCR) plate;

a second treatment module configured to treat a reagent, a tip, and a gene sample;

a sample injection module configured to inject an amplification reagent into a microwell of a PCR plate;

a purification treatment module configured to treat a gene sample;

an amplification detection module for gene amplification and detection;

a heat sealer configured to seal a PCR plate;

a material delivery module A;

a material delivery module B; and a material delivery module C, where the sample injection module and the first treatment module are arranged in the first mounting chamber A, the purification treatment module, the second treatment module, and the heat sealer are arranged in the first mounting chamber B, the amplification detection module is arranged in the first mounting chamber C, and the material delivery module A, the material delivery module B, and the material delivery module C are arranged in the second mounting chamber A, the second mounting chamber B, and the second mounting chamber C, respectively; the material delivery module A, the material delivery module B, and the material delivery module C are located below the sample injection module, the purification treatment module, and the amplification detection module, respectively; and during delivery, a PCR plate with an amplification reagent is allowed by the sample injection module to pass through the first switch door assembly A and reach a transferring function end of the material delivery module A; when the material delivery module A delivers the PCR plate to the second switch door assembly A, the PCR plate is placed at a transferring function end of the material delivery module B; when the material delivery module B delivers the PCR plate to the first switch door assembly B, the PCR plate enters the first mounting chamber B through the purification treatment module, and a purified gene sample is added to the PCR plate; the PCR plate is hot-sealed by the heat sealer; the purification treatment module places the PCR plate with the gene sample at the transferring function end of the material delivery module B through the first switch door assembly B; when the material delivery module B delivers the PCR plate to the second switch door assembly B, the PCR plate is placed at a transferring function end of the material delivery module C; and when the material delivery module C delivers the PCR plate to the first switch door assembly C, the PCR plate enters the first mounting chamber C through the purification treatment module, and the gene sample in the PCR plate is subjected to genetic testing by the amplification detection module.

The present disclosure has the following beneficial effects: the genetic testing device of the present disclosure can achieve the automatic pollution-free and efficient genetic testing and only a small part of a detection process of the genetic testing device involves manual operations with a low manual operation intensity.

REFERENCE NUMERALS IN THE ACCOMPANYING DRAWINGS

Figure 1:
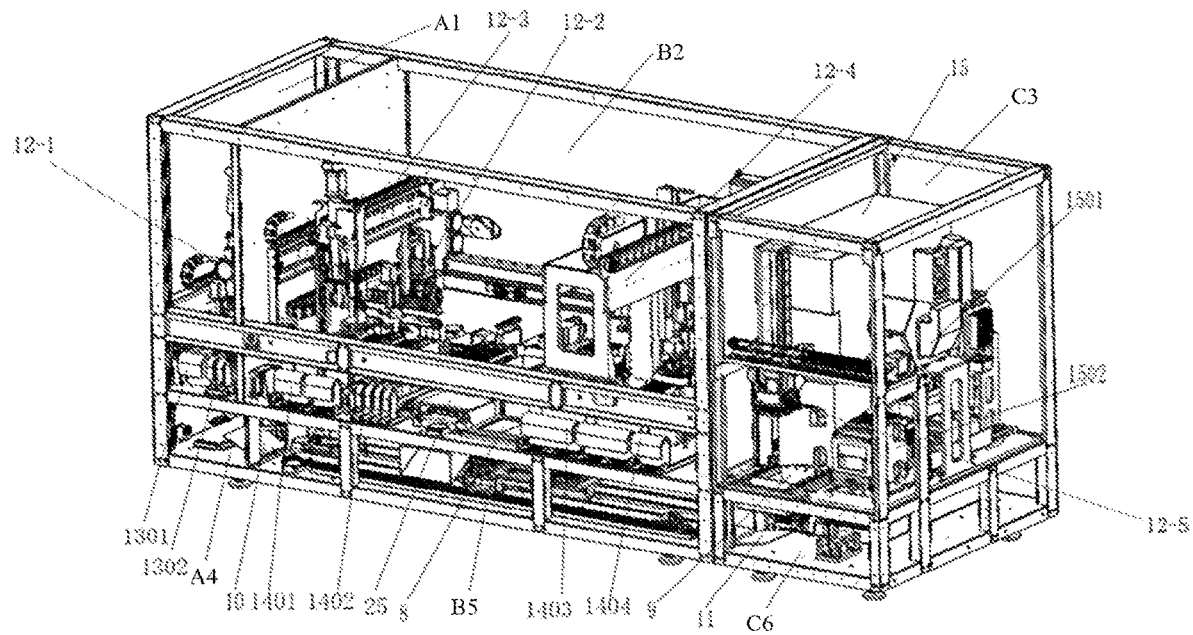
FIG. 1 is a schematic diagram illustrating a three-dimensional (3D) structure of the present disclosure.

A1 represents a first mounting chamber A, B2 represents a first mounting chamber B, C3 represents a first mounting chamber C, A4 represents a second mounting chamber A, B5 represents a second mounting chamber B, C6 represents a second mounting chamber C, 7 represents a first switch door assembly A, 8 represents a first switch door assembly B, 9 represents a first switch door assembly C, 10 represents a second switch door assembly A, 11 represents a second switch door assembly B, 18 represents a high-efficiency filter A, 19 represents an induced draft fan A, 22 represents a bracket, 23 represents a lifting mechanism B, 24 represents a translation component E, 26 represents a barcode scanner, 29 represents a pipette assembly B, and 30 represents a translation component I;

12-1, 12-2, 12-3, 12-4, and 12-5 represent transfer assemblies, 12-1-01, 12-2-01, and 12-3-01 represent X-direction moving components, 12-1-02, 12-2-02, and 12-3-02 represent Y-direction moving components, 12-1-03, 12-2-03, and 12-3-03 represent Z-direction moving components, 12-1-04, 12-2-04, and 12-3-04 represent pipette assemblies A, and 12-3-05 represents a gripper C; for the X-direction moving component 12-1-01 of transfer assembly 12-1, 12-1-01-1 represents a motor, 12-1-01-2 represents a driving pulley, 12-1-01-3 represents a driven pulley, 12-1-01-4 represents a drive belt, and 12-1-01-5 represents a mounting plate; for the Y-direction moving component 12-1-02 of transfer assembly 12-1, 12-1-02-1 represents a motor, 12-1-02-2 represents a driving pulley, 12-1-02-3 represents a driven pulley, 12-1-02-4 represents a drive belt, and 12-1-02-5 represents a mounting plate; for the Z-direction moving component 12-1-03 of transfer assembly 12-1, 12-1-03-1 represents a motor, 12-1-03-2 represents a lead screw nut mechanism, and 12-1-03-3 represents a mounting plate; for the X-direction moving component 12-2-01 of transfer assembly 12-2, 12-2-01-1 represents a motor, 12-2-01-2 represents a driving pulley, 12-2-01-3 represents a driven pulley, 12-2-01-4 represents a drive belt, and 12-2-01-5 represents a mounting plate; for the Y-direction moving component 12-2-02 of transfer assembly 12-2, 12-2-02-1 represents a motor, 12-2-02-2 represents a driving pulley, 12-2-02-3 represents a driven pulley, 12-2-02-4 represents a drive belt, and 12-2-02-5 represents a mounting plate; for the Z-direction moving component 12-2-03 of transfer assembly 12-2, 12-2-03-1 represents a motor, 12-2-03-2 represents a lead screw nut mechanism, and 12-2-03-3 represents a mounting plate;

13 represents a first treatment module, 1301 represents an arrangement rack A, 1302 represents an arrangement rack B, and 1303 represents a cooling module A;

14 represents a second treatment module, 1401 represents an arrangement rack C, 1402 represents an arrangement rack D, 1403 represents an arrangement rack E, 1404 represents an arrangement rack F, 1406 represents a heating module, 1408 represents an induced draft component, 1409 represents a spring leaf, 1410 represents an arrangement slot, 1411 represents a transposition, and 1412 represents a vibrating member A;

15 represents an amplification detection module, 1501 represents an optical detector, 1502 represents a heating base, 1503 represents a hot cover assembly, and 1504 represents a translation component C;

16-1 and 16-2 represent grippers A and 16-1-01 and 16-2-01 represent gripper control members A;

17 represents a purification module, 170-1 represents a heating oscillation chamber, 1702 represents a magnetic member, 1703 represents a translation component A, 1704 represents a reaction mounting rack, and 1705 represents a vibrating member B;

20 represents an opening-closing assembly, 2001 represents a lifting mechanism A, 2002 represents a gripper B, 2003 represents a fixing component A, 2004 represents a fixing component B, 2005 represents a translation component B, 2006 represents a snap ring, and 2007 represents a high-friction soft pad;

21 represents a translation component D, 2101 represents a motor D, 2102 represents a driving pulley D, 2103 represents a driven pulley D, 2104 represents a drive belt D, 2105 represents a mounting plate D, and 2106 represents a slide rail;

25 represents a solid-liquid waste discharge member, 2501 represents a translation component G, and 2502 represents a cover plate;

28 represents a heat sealing shell, 2801 represents a third switch door assembly, 2802 represents a heat sealer, 2803 represents a mounting plate F, and 2804 represents a translation component H; and

31 represents a liquid-receiving assembly; 3101 represents a liquid-receiving plate, 3102 represents a liquid-receiving groove, 3103 represents a mounting shaft, 3104 represents a liquid-receiving rack, 3105 represents a recess, 3106 represents a boss, and 3107 represents a torsion spring.

DETAILED DESCRIPTION OF THE EMBODIMENTS

To make the objectives, technical solutions, and advantages of the embodiments of the present disclosure clearer, the technical solutions in the embodiments of the present disclosure are clearly and completely described below with reference to the accompanying drawings in the embodiments of the present disclosure. Apparently, the described embodiments are merely some rather than all of the embodiments of the present disclosure. Generally, components of the embodiments of the present disclosure described and shown in the accompanying drawings may be arranged and designed in various manners.

Therefore, the following detailed description of the embodiments of the present disclosure in the accompanying drawings is not intended to limit the protection scope of the present disclosure, but merely indicates selected embodiments of the present disclosure. All other embodiments obtained by those of ordinary skill in the art based on the embodiments of the present disclosure without creative efforts should fall within the protection scope of the present disclosure.

It should be noted that similar reference signs and letters represent similar items in the accompanying drawings below. Therefore, once an item is defined in one accompanying drawing, it does not need to be further defined and described in subsequent accompanying drawings.

In the description of the present disclosure, it should be understood that orientation or position relationships indicated by terms "upper", "lower", "inner", "outer", "left", "right", and the like are orientation or position relationships shown in the accompanying drawings, or usual orientation or position relationships of the products of the present disclosure when in use, or orientation or position relationships commonly understood by those skilled in the art. These terms are only used to facilitate description of the present disclosure and simplify the description, but not to indicate or imply that the mentioned device or component must have a specific orientation or must be established and operated in a specific orientation, and thus these terms cannot be understood as a limitation to the present disclosure.

In addition, the terms such as "first" and "second" are used only for distinguishing description and cannot be understood as indicating or implying relative importance.

In the description of the present disclosure, it should be noted that, unless otherwise clearly specified and limited, the terms "arranged" and "connected" should be understood in a broad sense. For example, the "connection" may be a fixed connection, a removable connection, or an integral connection; may be a mechanical connection or an electrical connection; may be a direct connection or an indirect connection through an intermediate medium; or may be intercommunication between two components. Those of ordinary skill in the art may understand specific meanings of the above terms in the present disclosure based on a specific situation.

The specific implementations of the present disclosure will be described in detail below with reference to the accompanying drawings.

As shown in FIG. 1, a genetic testing device is provided, including: a safety cabinet, where the safety cabinet is divided into an upper part and a lower part; the upper part of the safety cabinet includes three independent mounting chambers, and a switch door assembly is provided between each mounting chamber of the upper part and the lower part of the safety cabinet; and the lower part of the safety cabinet also includes three mounting chambers that are provided with material delivery module A, material delivery module B, and material delivery module C, respectively.

The three mounting chambers of the upper part are first mounting chamber A1, first mounting chamber B2, and first mounting chamber C3; in the first mounting chamber A1, first treatment module 13 configured to treat an amplification reagent and a PCR plate and a sample injection module configured to inject an amplification reagent into a microwell of a PCR plate are provided; in the first mounting chamber B2, second treatment module 14 configured to treat a reagent, a tip, and a gene sample, a purification treatment module configured to treat a gene sample, and heat sealer 2802 configured to seal a PCR plate are provided; and in the first mounting chamber C3, amplification detection module 15 for gene amplification and detection is provided.

Further, a gas flow control system configured to control gas pressures of the first mounting chamber A1, the first mounting chamber B2, and the first mounting chamber C3 is provided in the three mounting chambers of the upper part.

The mounting chambers of the lower part are second mounting chamber A4, second mounting chamber B5, and second mounting chamber C6; the material delivery module A is arranged in the second mounting chamber A4 and is located below the sample injection module; the material delivery module B is arranged in the second mounting chamber B5 and is located below the purification treatment module; and the material delivery module C is arranged in the second mounting chamber C6 and is located below the amplification detection module 15.

Further, first switch door assembly A7 is provided between the first mounting chamber A1 and the second mounting chamber A4, first switch door assembly B8 is provided between the first mounting chamber B2 and the second mounting chamber B5, first switch door assembly C9 is provided between the first mounting chamber C3 and the second mounting chamber C6, second switch door assembly A10 is provided between the second mounting chamber A4 and the second mounting chamber B5, and second switch door assembly B11 is provided between the second mounting chamber B5 and the second mounting chamber C6.

When the genetic testing device of this embodiment works, a delivery process of a PCR plate is specifically as follows: a PCR plate with an amplification reagent is allowed by the sample injection module to pass through the first switch door assembly A7 and reach a transferring function end of the material delivery module A; when the material delivery module A delivers the PCR plate to the second switch door assembly A10, the PCR plate is placed at a transferring function end of the material delivery module B; when the material delivery module B delivers the PCR plate to the first switch door assembly B8, the PCR plate enters the first mounting chamber B2 through the purification treatment module, and a purified gene sample is added to the PCR plate; the PCR plate is hot-sealed by the heat sealer 2802; the purification treatment module places the PCR plate with the purified gene sample at the transferring function end of the material delivery module B through the first switch door assembly B8; when the material delivery module B delivers the PCR plate to the second switch door assembly B11, the PCR plate is placed at a transferring function end of the material delivery module C; and when the material delivery module C delivers the PCR plate to the first switch door assembly C9, the PCR plate enters the first mounting chamber C3 through the amplification detection module 15, and the gene sample in the PCR plate is subjected to genetic testing by the amplification detection module 15.

Figure 2:
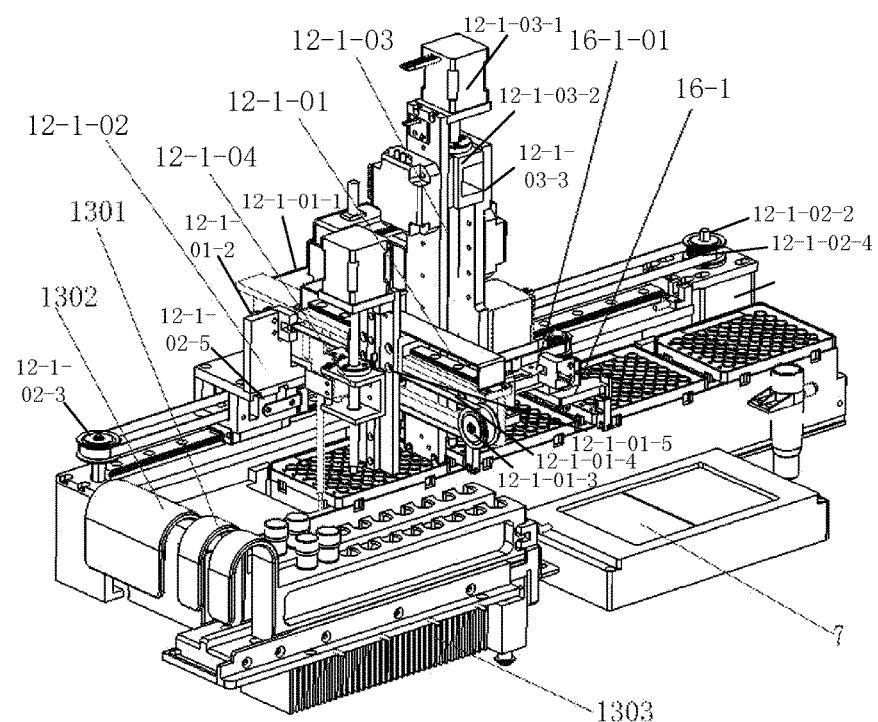
FIG. 2 is a schematic diagram illustrating a 3D structure of the sample injection module of the present disclosure.

As shown in FIG. 1 and FIG. 2, in the first mounting chamber A1, the sample injection module includes transfer assembly 12-1, gripper A16-1 configured to transfer a PCR plate, gripper control member A16-1-01 configured to control an open or close of the gripper A16-1, and pipette assembly A 12-1-04, where the transfer assembly 12-1 includes:

X-direction moving component 12-1-01 for X-direction movement, where the X-direction moving component includes motor A, driving pulley A, driven pulley A, drive belt A, and mounting plate A, the mounting plate A is fixedly connected to the drive belt A, a rotating shaft of the motor A is fixedly connected to a rotation center of the driving pulley A, and the driving pulley A and the driven pulley A are in a transmission connection through the drive belt A;

Y-direction moving component 12-1-02 for Y-direction movement, where the Y-direction moving component includes motor B, driving pulley B, driven pulley B, drive belt B, and mounting plate B, the mounting plate B is fixedly connected to the drive belt B, a rotating shaft of the motor B is fixedly connected to a rotation center of the driving pulley B, and the driving pulley B and the driven pulley B are in a transmission connection through the drive belt B; and Z-direction moving component 12-1-03 for Z-direction movement, where the Z-direction moving component includes motor C, lead screw nut mechanism A, and mounting plate C, a rotating shaft of the motor C is fixedly connected to lead screw A of the lead screw nut mechanism A, the mounting plate C is fixedly connected to nut A of the lead screw nut mechanism A, and the gripper control member A16-1-01 and the pipette assembly A 12-1-04 both are fixedly arranged on the mounting plate C, where the X-direction moving component 12-1-01 is arranged on the mounting plate B and the Z-direction moving component 12-1-03 is fixedly arranged on the mounting plate A.

In this embodiment, in the first mounting chamber A1: the sample injection module changes positions of the pipette assembly A 12-1-04 in the three directions of X, Y, and Z through the transfer assembly 12-1 to deliver an amplification reagent to a microwell of a PCR plate, and then an open or close of the gripper A16-1 is controlled by the gripper control member A16-1-01 to grab the PCR plate and make the PCR plate pass through the first switch door assembly A7 and reach the transferring function end of the material delivery module A.

As shown in FIG. 2, in the first mounting chamber A1, the first treatment module 13 includes at least two arrangement racks A1301, arrangement rack B1302, and cooling module A1303 configured to cool an amplification reagent; amplification reagents are placed on the arrangement racks A1301, and a number of amplification reagents on arrangement rack A1301 is no less than a number of amplification reagents required for an experiment on a set of gene samples; the PCR plate is placed on the arrangement rack B1302; an opening is formed at a side of the first mounting chamber A1; preferably, the opening of the first mounting chamber A1 is arranged in an X direction; the arrangement racks A1301 and the arrangement rack B1302 both are placed in the first mounting chamber A1 in a drawer-type manner; and the cooling module A1303 is arranged directly below the arrangement racks A1301.

In this embodiment, the first treatment module further includes a cleaning tank configured to clean the pipette assembly A 12-1-04 and after the pipette assembly A 12-1-04 conducts a pipetting operation for an amplification reagent, the transfer assembly 12-1 transfers a pipetting end of the pipette assembly A 12-1-04 to the cleaning tank, such that the pipetting end of the pipette assembly A 12-1-04 is cleaned and thus can be used for the next pipetting operation for an amplification reagent. At least two PCR plates are placed on the arrangement rack B1302, and the at least two arrangement racks A1301 are arranged to ensure that the sample injection can be conducted uninterruptedly without being affected by manual supplementation of an amplification reagent, which improves the efficiency of genetic testing.

As shown in FIG. 1, FIG. 3, FIG. 4, FIG. 5, FIG. 6, FIG. 9, and FIG. 10, in the first mounting chamber B2, the second treatment module 14 includes at least two arrangement racks C1401, at least two arrangement racks D1402, arrangement rack E1403, at least two temporary storage racks, arrangement rack F1404, vibrating member A1412 configured to vibrate a magnetic bead solution, heating module 1406 configured to heat a lysis buffer, and cooling module B configured to cool a purified gene sample; purification reagents, 8-tube strips for a purification reaction, and replacement tips A are placed on the arrangement racks C1401, and a number of purification reagents, a number of 8-tube strips, and a number of replacement tips A on arrangement rack C1401 are no less than a number of purification reagents, a number of 8-tube strips, and a number of replacement tips A required for an experiment on a set of gene samples, respectively; sample tubes with gene samples are placed on the arrangement racks D1402, and a number of gene samples on arrangement rack D1402 is no less than a number of gene samples required for an experiment on a set of gene samples; a cleaning solution for eluting a gene sample binding to a magnetic bead is placed on the arrangement rack E1403; replacement tip B and a sealing plate are placed on the arrangement rack F1404; the temporary storage racks are provided to receive PCR plates, and the cooling module B is arranged directly below the temporary storage racks; an opening is formed at a side of the first mounting chamber B2, and the opening is located at the same side as an opening of the first mounting chamber A1; the arrangement racks C1401, the arrangement racks D1402, the arrangement rack E1403, and the arrangement rack F1404 all are arranged in the first mounting chamber B2 in a drawer-type manner; and the second treatment module further includes transposition 1411 configured to receive an 8-tube strip in which gene samples will be added.

In this embodiment, the heating module 1406 is configured to heat a lysis buffer to avoid crystallization of the lysis buffer; a height of a first end of the heating module 1406 is lower than a height of a second end of the heating module 1406; when inserted into the first mounting chamber B2, the arrangement rack C1401 passes through the first and second ends of the heating module 1406 successively; the vibrating member A1412 can vibrate a magnetic bead solution, such that the magnetic bead solution is always in a homogeneous state to prevent a purification reaction from being affected by deposition; the at least two arrangement racks C1401, at least two arrangement racks D1402, arrangement rack E1403, at least two temporary storage racks, and arrangement rack F1404 are arranged, such that, when a nucleic acid extraction reagent or a consumable is manually supplemented, it can ensure that there is a corresponding spare product in the first mounting chamber B2 during the supplementation or replacement time to meet the use requirements of a purification reaction process or basically do not affect a purification reaction, and all processes of a purification reaction in the first mounting chamber B2 can be conducted uninterruptedly, thereby achieving the purpose of improving the efficiency of genetic testing.

Figure 6:
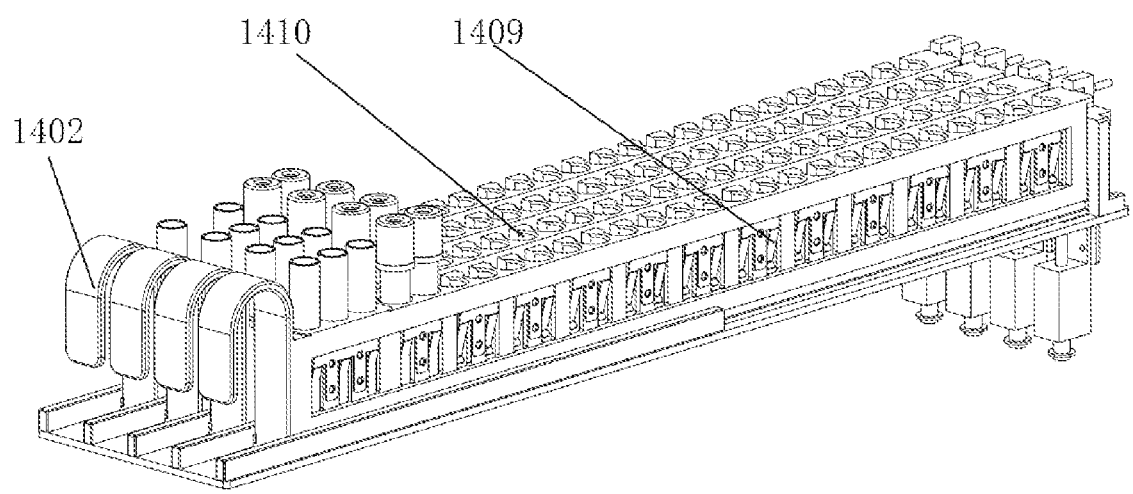
FIG. 6 is a schematic structural diagram of an arrangement rack D in the second treatment module of the present disclosure.

As shown in FIG. 6, the arrangement rack D1402 is provided with a plurality of arrangement slots 1410 configured to receive sample tubes; spring leaf 1409 is provided at a side of each of the arrangement slots 1410, and a reset direction of the spring leaf 1409 is towards a central axis of the arrangement slots 1410; and when a sample tube is placed in an arrangement slot 1410, the spring leaf 1409 is in pressing contact with a side wall of the sample tube.

In this embodiment, a sample tube is placed in arrangement slot 1410 of the arrangement rack D1402 in an insertion manner, and the arrangement slot is in pressing contact with a side wall of the sample tube through the spring leaf 1409 to fix the sample tube, which can prevent the sample tube from shaking during movement. The arrangement rack D1402 is provided with a plurality of barcodes, and arrangement slot 1410 is located between two adjacent barcodes; and the arrangement rack C1401 is also provided with a plurality of barcodes, and a test tube with a purification reagent is located between two adjacent barcodes. The genetic testing device further includes two barcode scanners 26 configured to scan and identify a barcode, and the specific locations and information of each sample tube and purification reagent are identified through the barcode scanners. An internal reference sample to determine whether a test result is correct is also placed on the arrangement rack D1402.

Figure 9:
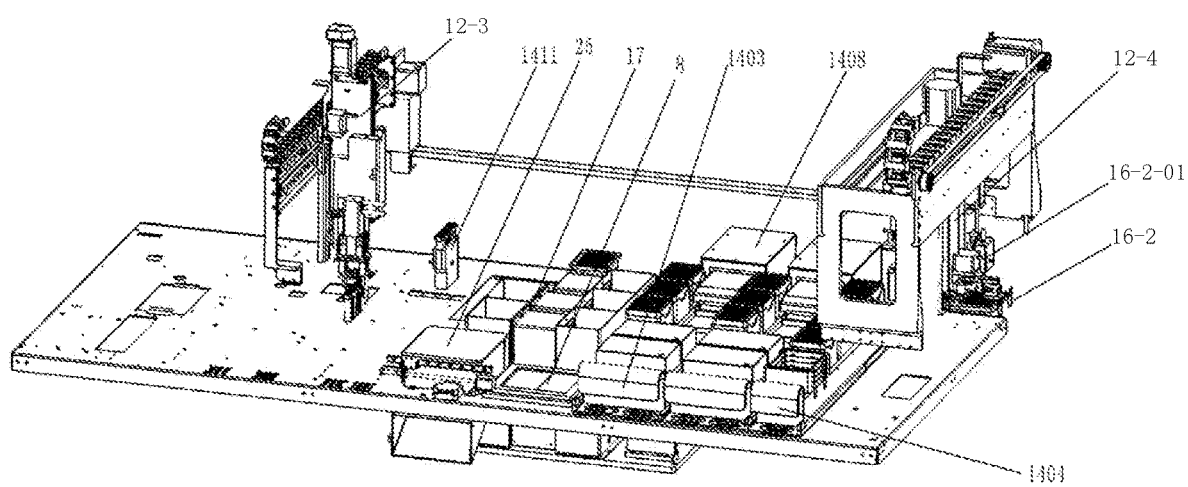
FIG. 9 is a schematic structural diagram 3 of the purification treatment module of the present disclosure.
Figure 10:
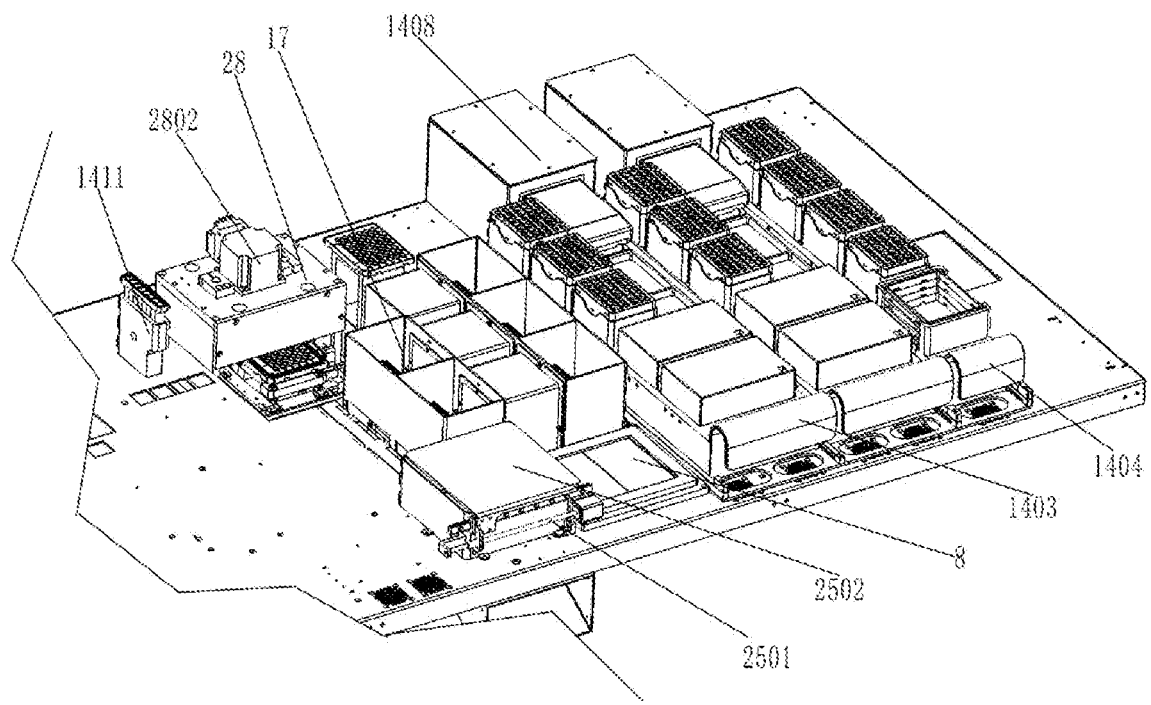
FIG. 10 is a schematic structural diagram 4 of the second treatment module of the present disclosure.
Figure 13:
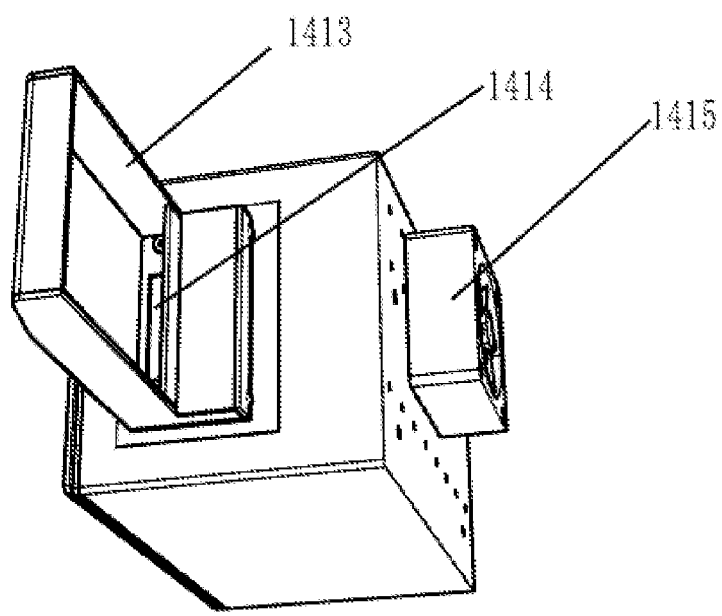
FIG. 13 is a schematic structural diagram of an induced draft component in the second treatment module of the present disclosure.

As shown in FIG. 9, FIG. 10, and FIG. 13, the second treatment module further includes at least two translation components F and at least two induced draft components 1408 configured to draw an aerosol generated by a gene sample; a translation component F is provided to change a distance between a gas inlet of an induced draft component 1408 and a temporary storage rack; and during induced draft, a gas inlet of an induced draft component 1408 is located directly above a temporary storage rack.

In this embodiment, the induced draft component includes high-efficiency filter C and induced draft fan D; a gas outlet of the high-efficiency filter C communicates with a gas inlet of the induced draft fan D; when a PCR plate with a gene sample is temporarily placed on the temporary storage rack, the translation component F makes a gas inlet of the high-efficiency filter C move such that the gas inlet is located directly above the PCR plate, and the induced draft fan D is started to draw an aerosol generated by the gene sample, which can prevent the first mounting chamber B2 from being contaminated by the aerosol.

As shown in FIG. 1, FIG. 3, FIG. 4, FIG. 9, and FIG. 10, in the first mounting chamber B2, the purification treatment module includes transfer assemblies 12-2, 12-3, and 12-4, and the transfer assemblies 12-2, 12-3, and 12-4 each include:

X-direction moving component 12-2-01/12-3-01/12-4-01 for X-direction movement, where the X-direction moving component includes motor A, driving pulley A, driven pulley A, drive belt A, and mounting plate A, the mounting plate A is fixedly connected to the drive belt A, a rotating shaft of the motor A is fixedly connected to a rotation center of the driving pulley A, and the driving pulley A and the driven pulley A are in a transmission connection through the drive belt A;

Y-direction moving component 12-2-02/12-3-02/12-4-02 for Y-direction movement, where the Y-direction moving component includes motor B, driving pulley B, driven pulley B, drive belt B, and mounting plate B, the mounting plate B is fixedly connected to the drive belt B, a rotating shaft of the motor B is fixedly connected to a rotation center of the driving pulley B, and the driving pulley B and the driven pulley B are in a transmission connection through the drive belt B; and Z-direction moving component 12-2-03/12-3-03/12-4-03 for Z-direction movement, where the Z-direction moving component includes motor C, lead screw nut mechanism A, and mounting plate C, a rotating shaft of the motor C is fixedly connected to lead screw A of the lead screw nut mechanism A, and the mounting plate C is fixedly connected to nut A of the lead screw nut mechanism A, where the Y-direction moving component is arranged on corresponding mounting plate A and the Z-direction moving component is fixedly arranged on corresponding mounting plate B.

Figure 3:
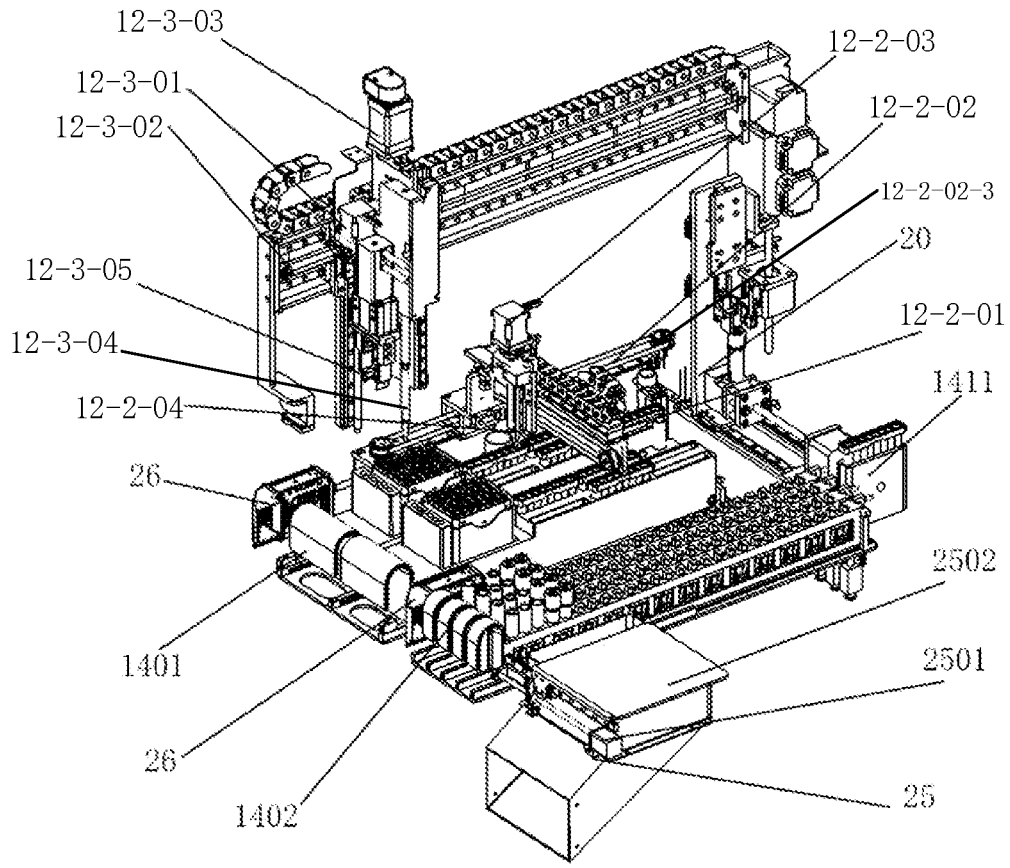
FIG. 3 is a schematic structural diagram 1 of the second treatment module of the present disclosure.
Figure 4:
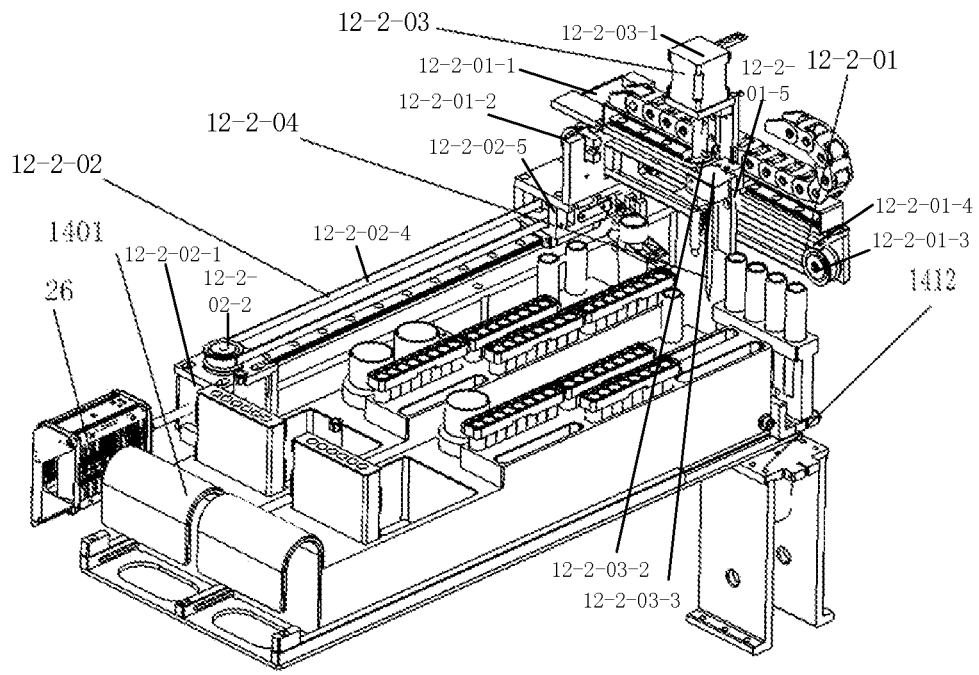
FIG. 4 is a schematic structural diagram 2 of the second treatment module of the present disclosure.
Figure 5:
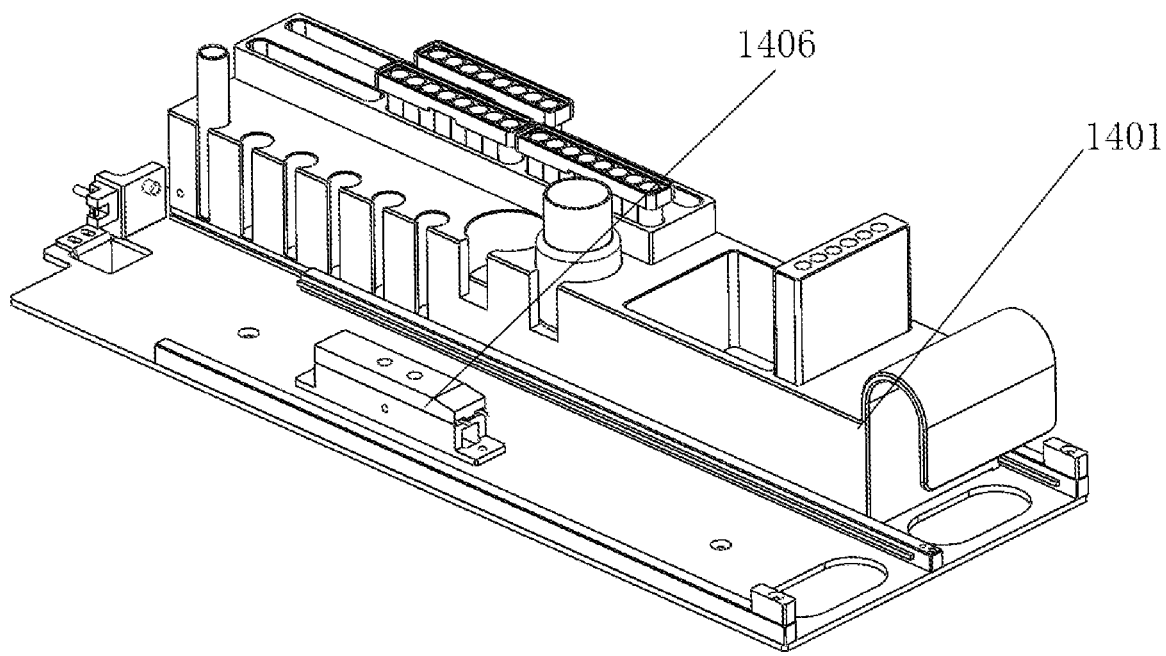
FIG. 5 is a schematic structural diagram of a heating module in the second treatment module of the present disclosure.

As shown in FIG. 3 and FIG. 4, the transfer assembly 12-2 is configured to transfer a purification reagent and includes pipette assembly A12-2-04, and the pipette assembly A12-2-04 is arranged on mounting plate C of the transfer assembly 12-2.

As shown in FIG. 3, the transfer assembly 12-3 is configured to transfer a gene sample, and includes pipette assembly A12-3-04, gripper C12-3-05 configured to transfer a sample tube and an 8-tube strip, and gripper control member C configured to control an open or close of the gripper C12-3-05, where the pipette assembly A12-3-04 and the gripper control member C are arranged on a mounting plate C of the transfer assembly 12-3.

As shown in FIG. 9, the transfer assembly 12-4 is configured to transfer a cleaning solution and includes pipette assembly A, gripper A16-2 configured to transfer a PCR plate, and gripper control member A16-2-01 configured to control an open or close of the gripper A16-2, where the pipette assembly A and the gripper control member A16-2-01 are arranged on mounting plate C of the transfer assembly 12-4.

In this embodiment, in the first mounting chamber B2, after a gene sample is subjected to a purification treatment by the purification treatment module, the purification treatment module controls an open or close of the gripper A16-2 through the gripper control member A16-2-01 to grab a PCR plate on the transferring function end of the material delivery module B and makes the PCR plate pass through the first switch door assembly B8 and reach the first mounting chamber B2, the purified gene sample is placed in a microwell of the PCR plate by the pipette assembly A, then the PCR plate with the gene sample is sealed with the sealing plate through the heat sealer 2802, and finally the PCR plate with the gene sample is allowed by the gripper A16-2 to pass through the first switch door assembly B8 and reach the transferring function end of the material delivery module B. In this embodiment, it can ensure that the three transfer assemblies 12-2, 12-3, and 12-4 do not interfere with each other during the entire purification process, and multiple sets of experiments can be conducted simultaneously, which shortens a time required by the purification process and improves the detection efficiency.

Preferably, the second treatment module further includes a cleaning tank configured to clean the pipette assembly A12-2-04 configured to transfer a purification reagent; after the pipette assembly A12-2-04 conducts a pipetting operation for a purification reagent, the transfer assembly 12-2 transfers a pipetting end of the pipette assembly A12-2-04 to the cleaning tank, such that the pipetting end of the pipette assembly A12-2-04 is cleaned and thus can be used for the next pipetting operation for a purification reagent; and the replacement tips A are provided to replace pipette assembly tips of the pipette assembly A12-3-04, and the replacement tips B are provided to replace pipette assembly tips of the pipette assembly A.

Figure 11:
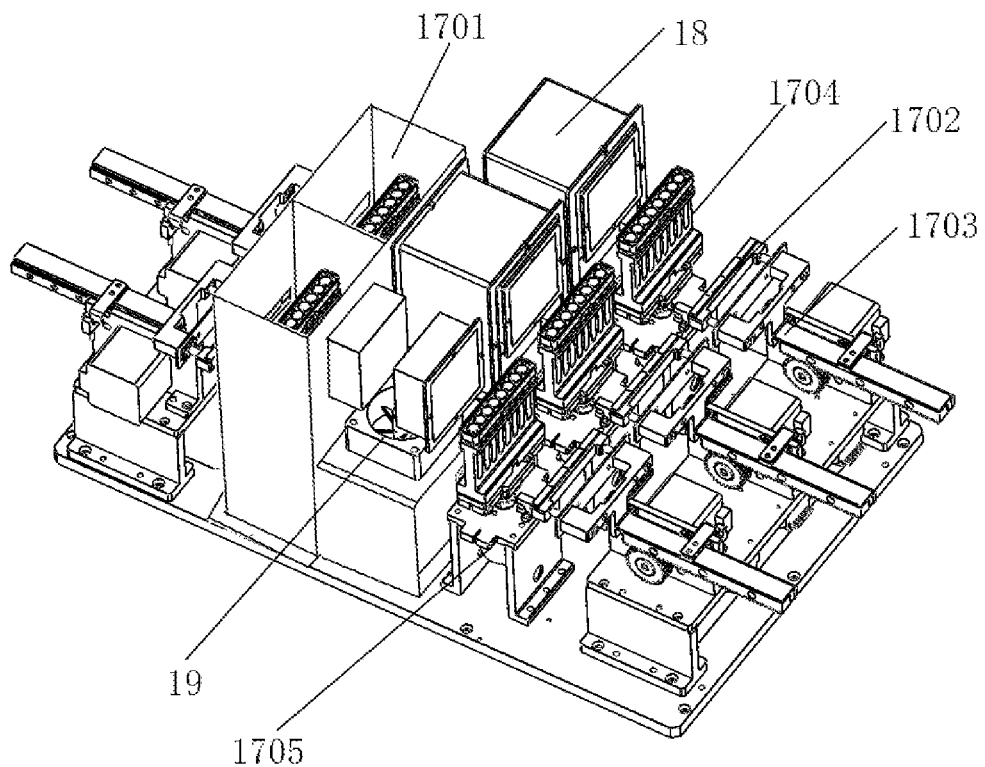
FIG. 11 is a schematic structural diagram of a purification module in the purification treatment module of the present disclosure.

As shown in FIG. 9, FIG. 10, and FIG. 11, in the first mounting chamber B2, the purification treatment module further includes at least one purification module 17, high-efficiency filter A18, and an induced draft fan A19; the purification module 17 includes heating oscillation chamber 1701, magnetic member 1702, vibrating member B1705, translation component A1703, and a heating member; the heating oscillation chamber 1701 is provided with reaction mounting rack 1704, and the 8-tube strips for the purification reaction are placed on the reaction mounting rack 1704; a heating function end of the heating member acts on the 8-tube strips, and the heating member is arranged at a vibrating function end of the vibrating member B1705; the translation component A1703 is configured to make the magnetic member 1702 move and change an attraction of the magnetic member 1702 to magnetic beads in the 8-tube strips; and a gas outlet is formed at a side of the heating oscillation chamber 1701, a gas inlet of the high-efficiency filter A18 communicates with the gas outlet of the heating oscillation chamber 1701, and a gas inlet of the induced draft fan A19 communicates with a gas outlet of the high-efficiency filter A18.

In this embodiment, an 8-tube strip is placed on the reaction mounting rack 1704, and then the heating member and the vibrating member B1705 are started, such that a gene sample in the 8-tube strip is heated for a purification treatment, and the vibrating member B1705 makes the gene sample in the 8-tube strip thoroughly mixed with a purification reagent. During a purification reaction, the induced draft fan A19 is started to make an aerosol generated during the purification reaction pass through a gas inlet of the high-efficiency filter A18, such that the aerosol is filtered by the high-efficiency filter A18; and when magnetic beads bind to a nucleic acid in the gene sample, the translation component A1703 makes the magnetic member 1702 move towards the 8-tube strip, the magnetic member 1702 adsorbs the magnetic beads in the 8-tube strip, and then a waste liquid is sucked out and discharged through the pipette assembly A such that the magnetic beads are separated from the waste liquid; and then the magnetic beads are subjected to elution to separate the nucleic acid in the gene sample from the magnetic beads, the magnetic member 1702 adsorbs the magnetic beads in the 8-tube strip, and the purified gene sample is transferred by the pipette assembly A to a PCR plate with an amplification reagent.

Figure 7:
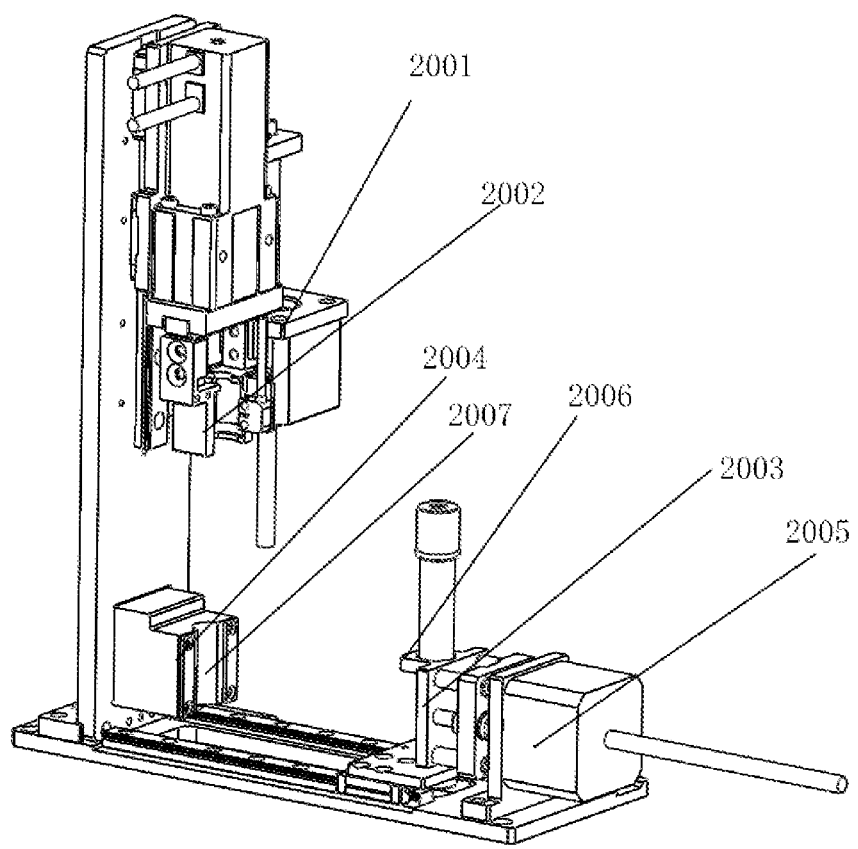
FIG. 7 is a schematic structural diagram of an opening-closing assembly in the second treatment module of the present disclosure.
Figure 8:
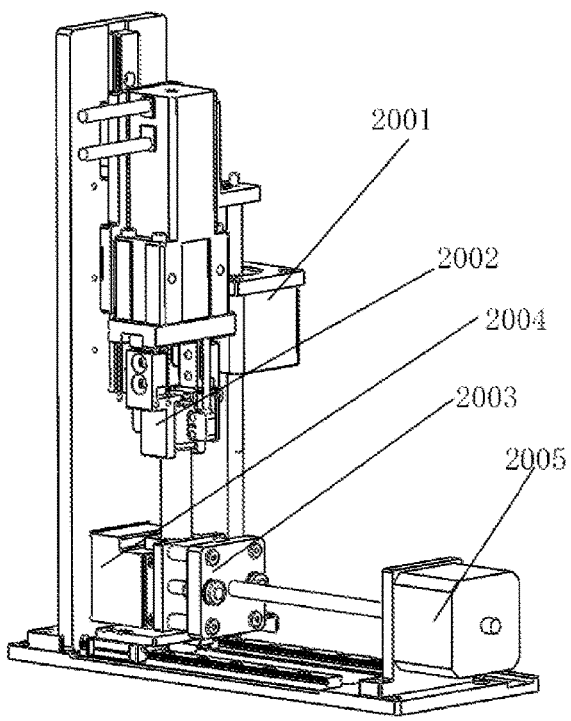
FIG. 8 is a schematic diagram of opening a tube cap by an opening-closing assembly in the purification treatment module of the present disclosure.

As shown in FIG. 3, FIG. 7, and FIG. 8, the purification treatment module further includes opening-closing assembly 20 configured to open or close a tube cap of a sample tube; the opening-closing assembly includes lifting mechanism A2001, gripper B2002, gripper control member B configured to control an open or close of the gripper B2002, and a tube body-fixing member configured to fix a tube body of a sample tube; a lifting function end of the lifting mechanism A2001 acts on the gripper B2002; and the tube body-fixing member is arranged below the gripper B2002.

In this embodiment, a sample tube is fixed by the tube body-fixing member, open degree of the gripper B2002 is increased by the gripper control member B, the lifting mechanism A2001 makes the gripper control member B and the gripper B2002 descend to a tube cap of the sample tube, the gripper control member B reduces an open degree of the gripper B2002 to make the gripper B2002 clamp the tube cap, and then the lifting mechanism A2001 makes the gripper control member B and the gripper B2002 ascend to open the tube cap; and a reverse process is a cap-closing operation process.

As shown in FIG. 3, FIG. 7, and FIG. 8, the tube body-fixing member includes fixing component A2003, fixing component B2004, and translation component B2005 configured to control a distance between the fixing component A2003 and the fixing component B2004; the fixing component B2004 is arranged directly below the gripper B2002; a moving function end of the translation component B2005 acts on the fixing component A2003; and opposite sides of the fixing component A2003 and the fixing component B2004 are arc surfaces, and an upper end of the arc surface of the fixing component A2003 is provided with a snap ring 2006 configured to snap a sample tube.

In this embodiment, a sample tube is taken out by the transfer assembly 12-3 from the arrangement slot of the arrangement rack D1402 and then transferred to the snap ring 2006 above the fixing component A2003, and then the translation component B2005 makes the fixing component A2003 move such that side walls of the sample tube is in pressing contact with the arc surfaces of the fixing component A2003 and the fixing component B2004, respectively, thereby achieving the purpose of fixing the sample tube; and after a tube cap is opened and a gene sample is taken out, the tube cap is closed, the translation component B2005 makes the fixing component A2003 move away from the fixing component B2004, and finally the sample tube is placed by the transfer assembly 12-3 in the corresponding arrangement slot of the arrangement rack D1402.

As shown in FIG. 7, the arc surfaces of the fixing component A2003 and the fixing component B2004 each are fixedly provided with a high-friction soft pad 2007.

In this embodiment, the arc surfaces of the fixing component A2003 and the fixing component B2004 each are fixedly provided with a high-friction soft pad 2007 to enhance a pressing interaction between a sample tube and the fixing component A2003 or the fixing component B2004 when the sample tube is fixed and to enhance a fixation effect for a sample tube.

Figure 14:
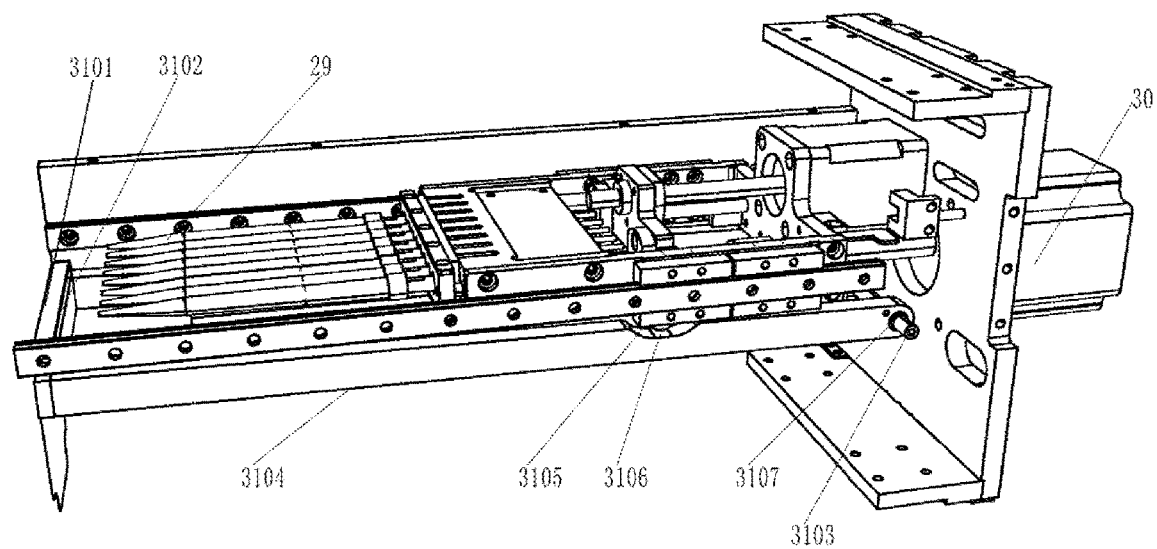
FIG. 14 is a schematic structural diagram of a pipette assembly B in the purification treatment module of the present disclosure.
Figure 15:
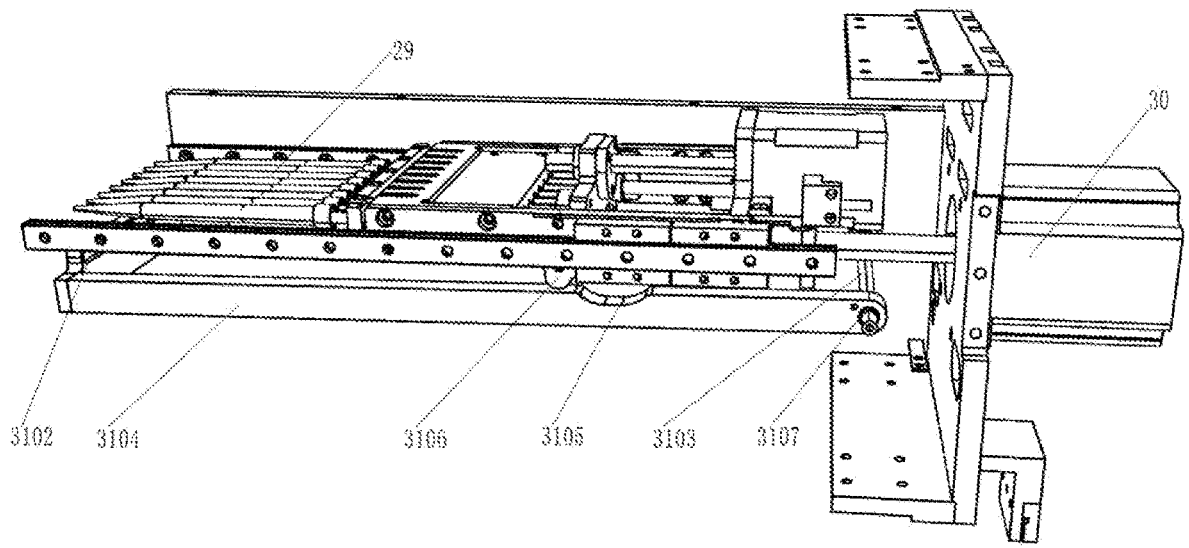
FIG. 15 is a schematic diagram of use of a pipette assembly B in the purification treatment module of the present disclosure.

As shown in FIG. 14 and FIG. 15, the purification treatment module further includes pipette assembly B29 for micropipetting, a translation component 130, and a liquid-receiving assembly configured to receive a liquid from the pipette assembly B29; the liquid-receiving assembly includes liquid-receiving plate 3101, mounting shaft 3103, liquid-receiving rack 3104, and a rotation-driving member configured to drive the liquid-receiving rack 3104 to rotate; liquid-receiving groove 3102 is formed on the liquid-receiving plate 3101; the mounting shaft 3103 and the translation component 130 are arranged on the same mounting plate C as the gripper control member A1601; a first end of the liquid-receiving rack 3104 is rotatably arranged on the mounting shaft 3103, and a second end of the liquid-receiving rack 3104 is fixedly connected to the liquid-receiving plate 3101; the translation component 130 is configured to change relative positions of the liquid-receiving plate 3101 and the pipette assembly B29 in a dropping direction of a pipette assembly tip; and specifically, the pipette assembly B29 is the pipette assembly A in the transfer assembly 12-4 in the above embodiment.

In this embodiment, for micropipetting, the translation component 130 and the rotation-driving member both are started, the pipette assembly B29 moves in a dropping direction relative to the liquid-receiving plate 3101, and the rotation-driving member drives the liquid-receiving rack 3104 to rotate and drives the liquid-receiving plate 3101 to rotate away from the pipette assembly B29; and for liquid-receiving, the translation component 130 and the rotation-driving member both are started, the translation component 130 moves in a direction opposite to the dropping direction relative to the liquid-receiving plate 3101, the rotation-driving member drives the liquid-receiving rack 3104 to rotate and drives the liquid-receiving plate 3101 to rotate towards the pipette assembly B29, and when rotating to a specified place, the liquid-receiving groove 3102 of the liquid-receiving plate 3101 is located directly below a tip of the pipette assembly B29 to collect a liquid dropping from the pipette assembly B29.

As shown in FIG. 14 and FIG. 15, the rotation-driving member includes recess 3105, boss 3106, and torsion spring 3107; the recess 3105 is formed on the liquid-receiving rack 3104, the boss 3106 is fixedly arranged on the pipette assembly B29, and the boss 3106 is always in pressing contact with the liquid-receiving rack 3104; a first end of the torsion spring 3107 is fixedly connected to the first end of the liquid-receiving rack 3104, and a second end of the torsion spring 3107 is fixedly connected to the mounting shaft 3103; and the torsion spring 3107 is always in an energy storage state.

In this embodiment, for micropipetting, the translation component 130 is started, the pipette assembly B29 moves in a dropping direction relative to the liquid-receiving plate 3101, and the boss 3106 moves away from the recess 3105 of the liquid-receiving rack 3104, such that a distance between the pipette assembly B29 and the liquid-receiving rack 3104 increases; and since the liquid-receiving rack 3104 is rotatably arranged on the mounting shaft 3103, the liquid-receiving rack 3104 drives the liquid-receiving plate 3101 to rotate away from the pipette assembly B29, such that the liquid-receiving plate 3101 moves to be no longer below the tip of the pipette assembly B29, the pipette assembly B29 can conduct a normal pipetting operation, and the torsion spring 3107 continues to store energy through further deformation; and for liquid-receiving, the translation component 130 is started, the pipette assembly B29 moves in a direction opposite to a dropping direction relative to the liquid-receiving plate 3101, and the boss 3106 moves towards the recess 3105 of the liquid-receiving rack 3104, such that a distance between the pipette assembly B29 and the liquid-receiving rack 3104 decreases, a pressing interaction between the boss 3106 and the liquid-receiving rack 3104 decreases, and the torsion spring 3107 releases energy through deformation recovery to drive the liquid-receiving rack 3104 to rotate and drive the liquid-receiving plate 3101 to rotate towards the pipette assembly B29; and when rotating to a specified place, the boss 3106 is located in the recess 3105 of the liquid-receiving rack 3104, and the liquid-receiving groove 3102 of the liquid-receiving plate 3101 is located directly below a tip of the pipette assembly B29 to collect a liquid dropping from the pipette assembly B29, which prevents the liquid in the pipette assembly B29 from dropping to cause contamination to the sample and genetic testing device during operation.

In some embodiments, the rotation-driving member includes a gear wheel and a gear rack, the gear wheel is fixedly arranged on the first end of the liquid-receiving rack 3104, the gear wheel can mesh with the gear rack for transmission, and the gear rack is fixedly arranged on the pipette assembly B29.

For micropipetting, the translation component 130 is started, the pipette assembly B29 moves in a dropping direction relative to the liquid-receiving plate 3101, the gear rack moves with the pipette assembly B29, and the gear rack meshes with the gear wheel to drive the liquid-receiving rack 3104 and the liquid-receiving plate 3101 to rotate away from the pipette assembly B29, such that the liquid-receiving plate 3101 moves to be no longer below the tip of the pipette assembly B29 and the pipette assembly B29 can conduct a normal pipetting operation; and for liquid-receiving, the translation component 130 is started, the pipette assembly B29 moves in a direction opposite to a dropping direction relative to the liquid-receiving plate 3101, the gear rack moves with the pipette assembly B29 in the opposite direction, and the gear rack meshes with the gear wheel to drive the liquid-receiving rack 3104 and the liquid-receiving plate 3101 to rotate towards the pipette assembly B29; and when rotating to a specified place, the liquid-receiving groove 4 of the liquid-receiving plate 3101 is located directly below a tip of the pipette assembly B29 to collect a liquid dropping from the pipette assembly B29, which prevents the liquid in the pipette assembly B29 from dropping to cause contamination to the sample and genetic testing device during operation.

As shown in FIG. 1, in the first mounting chamber C3, the amplification detection module includes transfer assembly 12-5, gripper A configured to transfer a PCR plate, and a gripper control member A configured to control an open or close of the gripper A, where the transfer assembly 12-5 includes: an X-direction moving component for X-direction movement, where the X-direction moving component includes motor A, driving pulley A, driven pulley A, drive belt A, and mounting plate A, the mounting plate A is fixedly connected to the drive belt A, a rotating shaft of the motor A is fixedly connected to a rotation center of the driving pulley A, and the driving pulley A and the driven pulley A are in a transmission connection through the drive belt A; a Y-direction moving component for Y-direction movement, where the Y-direction moving component includes motor B, driving pulley B, driven pulley B, drive belt B, and mounting plate B, the mounting plate B is fixedly connected to the drive belt B, a rotating shaft of the motor B is fixedly connected to a rotation center of the driving pulley B, and the driving pulley B and the driven pulley B are in a transmission connection through the drive belt B; and a Z-direction moving component for Z-direction movement, where the Z-direction moving component includes motor C, lead screw nut mechanism A, and mounting plate C, a rotating shaft of the motor C is fixedly connected to lead screw A of the lead screw nut mechanism A, the mounting plate C is fixedly connected to nut A of the lead screw nut mechanism A, and the gripper control member A and is fixedly arranged on the mounting plate C; and the X-direction moving component is arranged on the mounting plate B and the Z-direction moving component is fixedly arranged on the mounting plate A.

In this embodiment, in the first mounting chamber C3: the amplification detection module 15 controls an open or close of the gripper A through the gripper control member A to grab a PCR plate at a transferring function end of the material delivery module C and makes the PCR plate pass through the first switch door assembly C9 and reach the first mounting chamber C3, and then a gene sample is subjected to amplification and optical detection by the amplification detection module 15.

Figure 16:
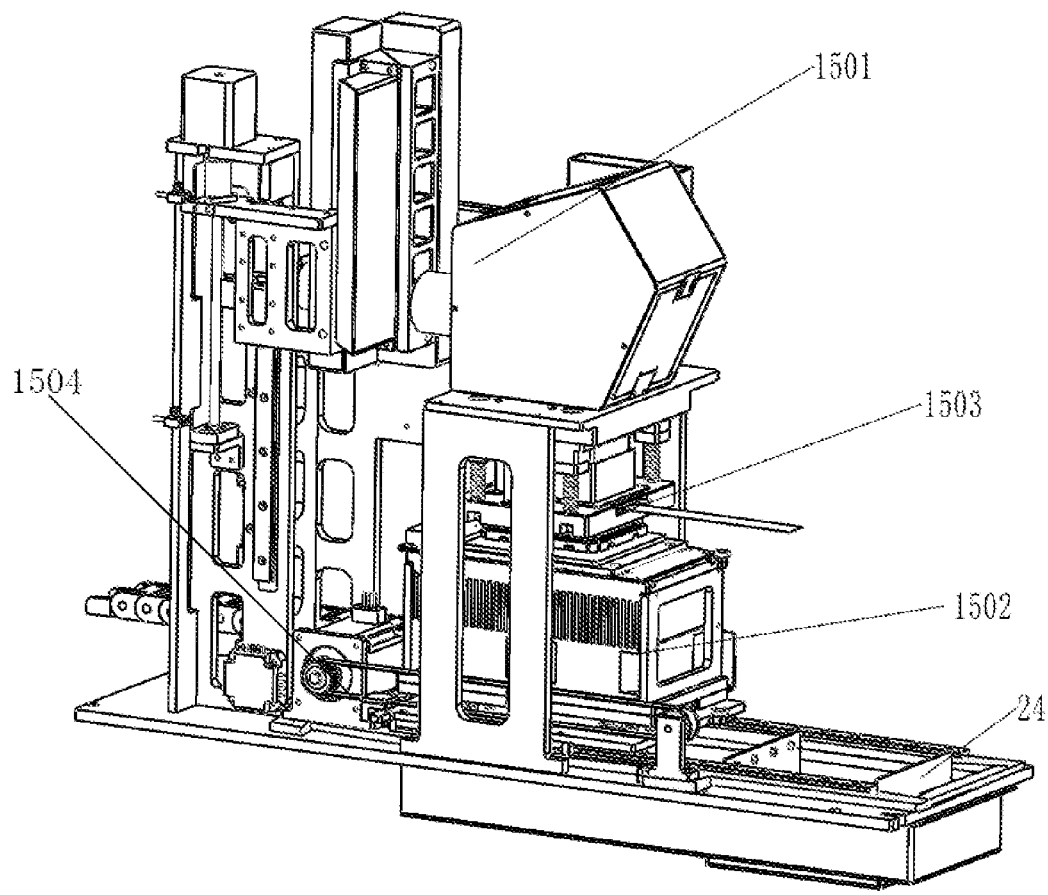
FIG. 16 is a schematic structural diagram of the amplification detection module of the present disclosure.
Figure 17:
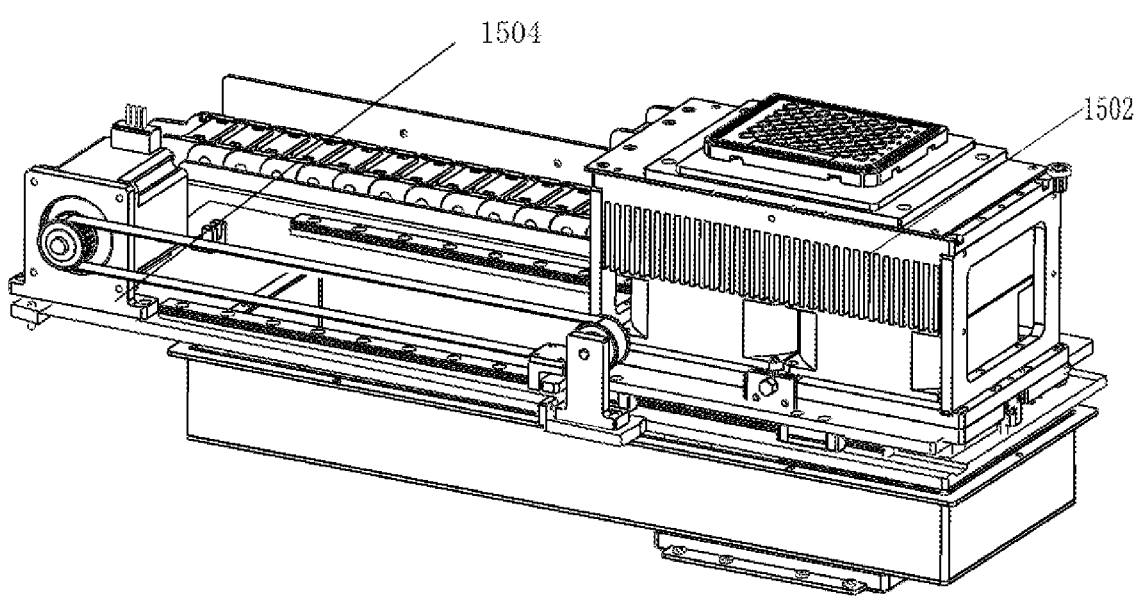
FIG. 17 is a schematic structural diagram of a translation component C in the amplification detection module of the present disclosure.

As shown in FIG. 1, FIG. 16, and FIG. 17, the amplification detection module further includes at least two metal bath modules, at least two optical detectors 1501, and at least two translation components C1504; each metal bath module includes hot cover assembly 1503 and heating base 1502; a hot cover assembly 1503 is arranged at a detection port of an optical detector 1501; and a moving function end of a translation component C1504 acts on heating base 1502.

In this embodiment, the transfer assembly 12-5 transfers a PCR plate at a transferring function end of the material delivery module C to the heating base 1502, the translation component C1504 makes the heating base 1502 move such that the PCR plate is located directly below the hot cover assembly 1503, then the purified gene sample is subjected to amplification in a metal bath, and an amplified gene sample is subjected to optical detection and analysis by the optical detector 1501; and after the amplification detection is completed, the translation component C1504 makes the heating base 1502 move such that the PCR plate is removed and separated from the heating base 1502 by the transfer assembly 12 and gripper A, and a waste is discharged.

Figure 18:
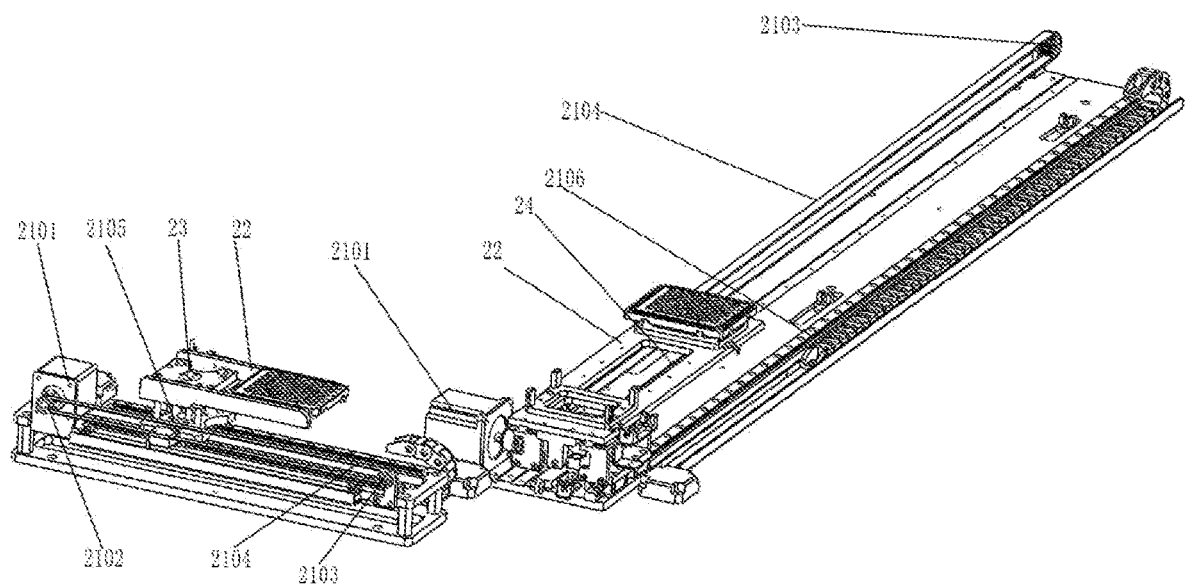
FIG. 18 is a schematic structural diagram of the material delivery module A and the material delivery module B of the present disclosure.
Figure 19:
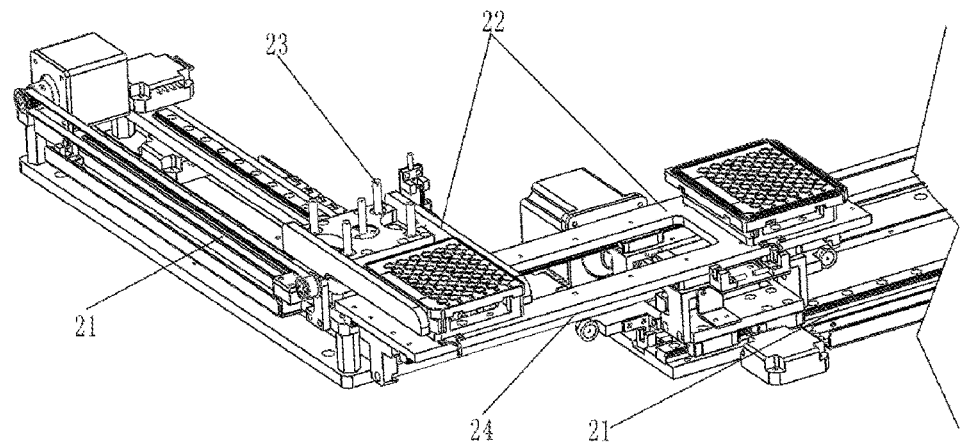
FIG. 19 is a schematic diagram of the material delivery module A and the material delivery module B of the present disclosure during delivery.

As shown in FIG. 18 and FIG. 19, the material delivery module A includes bracket 22 configured to receive a PCR plate and translation component D21; the translation component D21 includes motor D2101, slide rail 2106, driving pulley D2102, driven pulley D2103, drive belt D2104, and mounting plate D2105, where the mounting plate D2105 is fixedly connected to the drive belt D2104, a rotating shaft of the motor D2101 is fixedly connected to a rotation center of the driving pulley D2102, the driving pulley D2102 and the driven pulley D2103 are in a transmission connection through the drive belt D2104, the mounting plate D2105 is slidably arranged in the slide rail 2106, and the slide rail 2106 is fixedly arranged in a mounting chamber; further, the material delivery module A further includes lifting mechanism B23 configured to adjust a height of the bracket 22, and the lifting mechanism B23 is fixedly arranged on the mounting plate D2105; and the bracket of the material delivery module A is further provided with a locking member, a recess is formed on each of the PCR plate and the sealing plate, and the bracket of the material delivery module A achieves the purpose of receiving a PCR plate through the locking member and the recess.

As shown in FIG. 18, FIG. 19, FIG. 20, and FIG. 21, the material delivery module B includes bracket 22 configured to receive a PCR plate and translation component D21; the translation component D21 includes motor D2101, slide rail 2106, driving pulley D2102, driven pulley D2103, drive belt D2104, and mounting plate D2105, where the mounting plate D2105 is fixedly connected to the drive belt D2104, a rotating shaft of the motor D2101 is fixedly connected to a rotation center of the driving pulley D2102, the driving pulley D2102 and the driven pulley D2103 are in a transmission connection through the drive belt D2104, the mounting plate D2105 is slidably arranged in the slide rail 2106, and the slide rail 2106 is fixedly arranged in a mounting chamber; and further, the material delivery module B further includes translation component E24 configured to make the bracket 22 move, the translation component E24 is fixedly arranged on the mounting plate D2105, and two ends of the bracket of the material delivery module B are configured to receive a PCR plate with an amplification reagent and a PCR plate with a gene sample, respectively.

Figure 20:
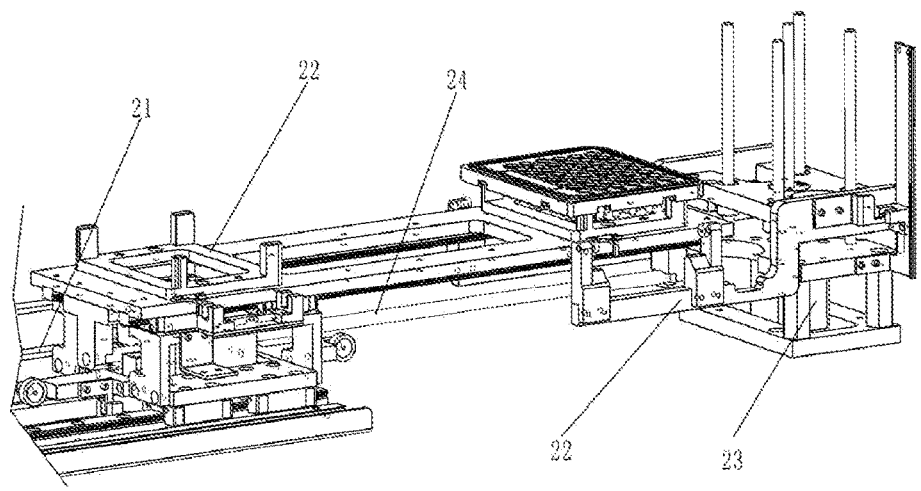
FIG. 20 is a schematic diagram of the material delivery module B and the material delivery module C of the present disclosure before delivery.
Figure 21:
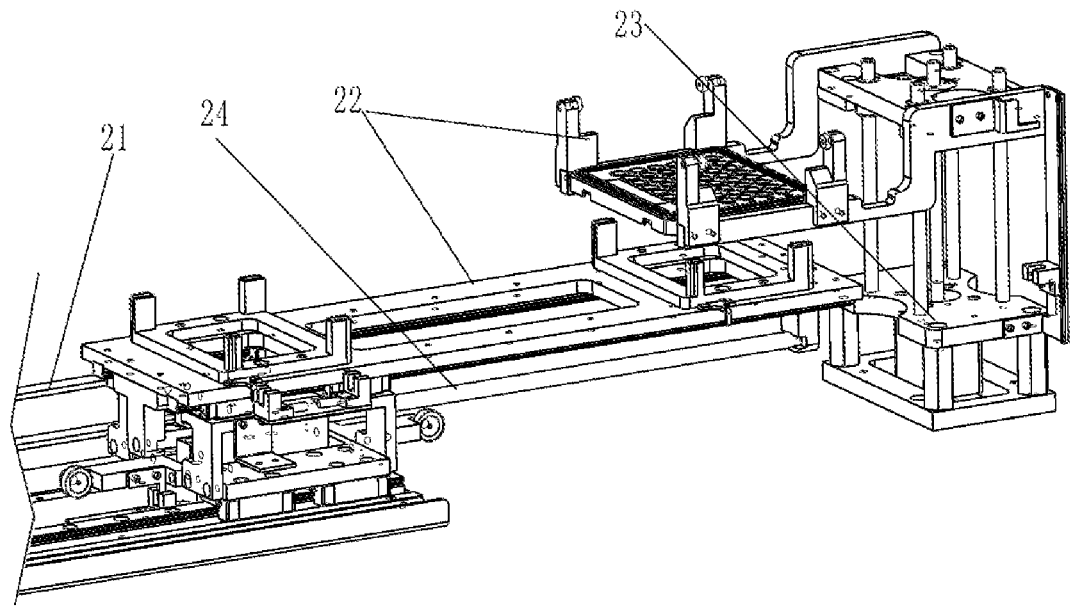
FIG. 21 is a schematic diagram of the material delivery module B and the material delivery module C of the present disclosure after delivery.

As shown in FIG. 20 and FIG. 21, the material delivery module C includes bracket 22 configured to receive a PCR plate and lifting mechanism B23 configured to adjust a height of the bracket 22; and the bracket of the material delivery module C is further provided with a locking member, a recess is formed on each of the PCR plate and the sealing plate, and the bracket of the material delivery module C achieves the purpose of receiving a PCR plate through the locking member and the recess.

During delivery, at the second switch door assembly A, the material delivery module A delivers a PCR plate with an amplification reagent to the material delivery module B; and at the second switch door assembly B, the material delivery module B delivers a PCR plate with a gene sample to the material delivery module C, and a lifting function end of the lifting mechanism B of the material delivery module C is located directly below the first switch door assembly C9.

A transfer process between the material delivery module A and the material delivery module B is as follows: A first end of the bracket of the material delivery module B is transferred by the translation component D21 and the translation component E24 to the second mounting chamber A4, the bracket of the material delivery module A receives a PCR plate, a height of the bracket of the material delivery module A is increased by the lifting mechanism B23 such that the bracket of the material delivery module A is located above the bracket of the material delivery module B, then the translation component D21 makes the PCR plate move and makes the bracket of the material delivery module B located directly below the bracket of the material delivery module A, and then the height of the bracket of the material delivery module A is decreased by the lifting mechanism B23 of the material delivery module A, such that the PCR plate is transferred from the material delivery module A to the material delivery module B.

A transfer process between the material delivery module B and the material delivery module C is as follows: A height of the bracket of the material delivery module C is decreased by the lifting mechanism B23 of the material delivery module C such that the bracket of the material delivery module C is located below the bracket of the material delivery module B, a second end of the bracket of the material delivery module C is transferred by the translation component D21 and the translation component E24 to the second mounting chamber C6 such that the second end of the bracket of the material delivery module B is located directly above the bracket of the material delivery module C, and then the height of the bracket of the material delivery module C is increased by the lifting mechanism B23 of the material delivery module C, such that the PCR plate is transferred from the material delivery module B to the material delivery module C.

Figure 22:
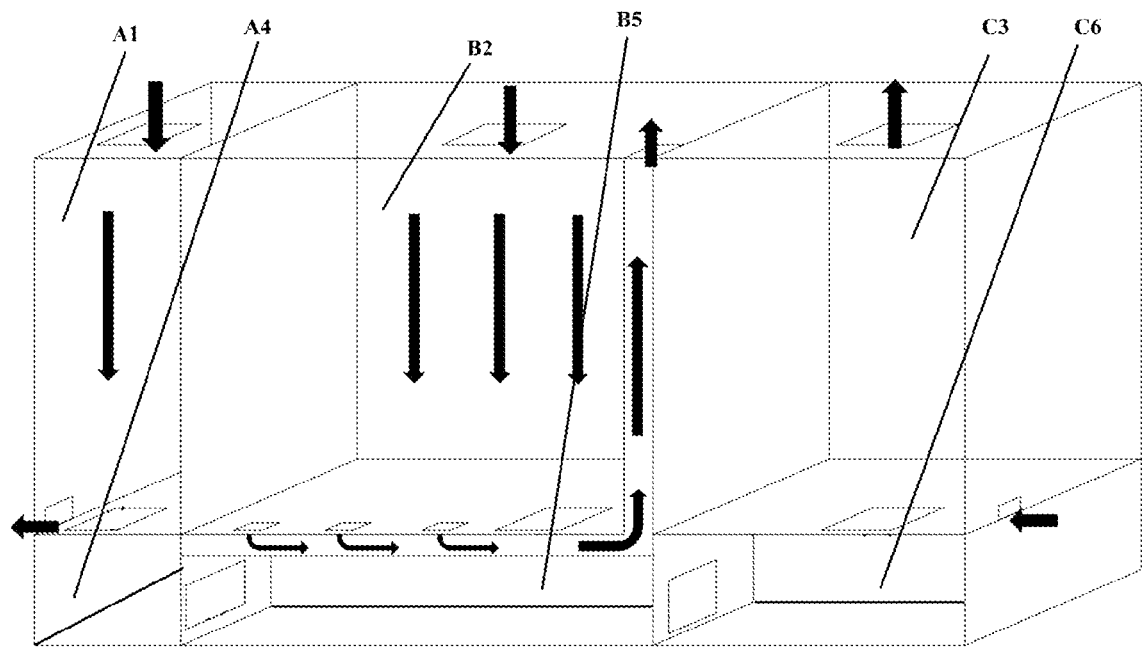
FIG. 22 is a schematic diagram illustrating a gas flow direction of the gas flow control system of the present disclosure.

As shown in FIG. 22, the gas flow control system includes three gas flow members configured to control internal gas pressures of the first mounting chamber A1, the first mounting chamber B2, and the first mounting chamber C3, respectively; each gas flow member includes an induced draft fan B and an induced draft fan C; a gas outlet of the induced draft fan B communicates with a gas inlet of a mounting chamber, a gas inlet of the induced draft fan C communicates with a gas outlet of a mounting chamber, and a gas inlet of the induced draft fan B and the gas inlet of the induced draft fan C each are provided with a high-efficiency filter B; and gas pressures of the first mounting chamber A1, the first mounting chamber B2, and the first mounting chamber C3 decrease sequentially, a gas pressure of the first mounting chamber A1 is greater than a gas pressure outside the safety cabinet, and a gas pressure of the first mounting chamber C3 is smaller than the gas pressure outside the safety cabinet.

In this embodiment, the gas inlet of the induced draft fan B and the gas inlet of the induced draft fan C each are provided with high-efficiency filter B to prevent air pollution, and speeds of the induced draft fan B and the induced draft fan C both are adjustable; and when pressures of the first mounting chamber A1, the first mounting chamber B2, and the first mounting chamber C3 are controlled, it is necessary to ensure that the pressures of the first mounting chamber A1, the first mounting chamber B2, and the first mounting chamber C3 decrease by 5 KPa to 20 KPa sequentially, a gas pressure of the first mounting chamber A1 is greater than a gas pressure outside the safety cabinet, and a gas pressure of the first mounting chamber C3 is smaller than a gas pressure outside the safety cabinet.

In addition, when a high-risk virus needs to tested, it is necessary to prevent air in the first mounting chamber B2 of the genetic testing device from polluting external air to protect the safety of a tester, and the speeds of the induced draft fan B and the induced draft fan C are adjusted to make a gas pressure of the first mounting chamber B2 smaller than a gas pressure outside the safety cabinet; and when the arrangement rack C1401, the arrangement rack D1402, the arrangement rack E1403, and the arrangement rack F1404 are pulled, the external air flows into the device through the opening of the first mounting chamber B2, but an exhaust fan for air discharge is provided at the opening of the first mounting chamber B2, and the exhaust fan can discharge the external air, such that the first mounting chamber B2 will not be polluted. When a high-sensitivity test needs to be conducted, it is necessary to prevent the external air from polluting the first mounting chamber B2 of the genetic testing device, and the speeds of the induced draft fan B and the induced draft fan C are adjusted to make a gas pressure of the first mounting chamber B2 larger than a gas pressure outside the safety cabinet, thereby avoiding the inflow of air.

As shown in FIG. 1, FIG. 3, and FIG. 10, the genetic testing device further includes solid-liquid waste discharge member 25 arranged in the first mounting chamber B2; the solid-liquid waste discharge member 25 includes a solid waste discharge chamber configured to discharge a solid waste, a liquid waste discharge chamber configured to discharge a liquid waste, translation component G2501, and cover plate 2502; a moving function end of the translation component G2501 acts on the cover plate 2502; and the cover plate 2502 covers upper ends of the liquid waste discharge chamber and the solid waste discharge chamber.

In this embodiment, when the replacement tip A and the replacement tip B are discharged as a waste, the translation component G2501 makes the cover plate 2502 move such that the solid waste discharge chamber is open, the replacement tip A and the replacement tip B can be discharged to the solid waste discharge chamber, and after the discharge is completed, the translation component G2501 makes the cover plate 2502 move in an opposite direction to close the solid waste discharge chamber; and when a liquid waste is discharged, the translation component G2501 makes the cover plate 2502 move such that the liquid waste discharge chamber is open, the pipette assembly A discharges the liquid waste into the liquid waste discharge chamber, and after the discharge is completed, the translation component G2501 makes the cover plate 2502 move in an opposite direction to close the liquid waste discharge chamber.

Figure 12:
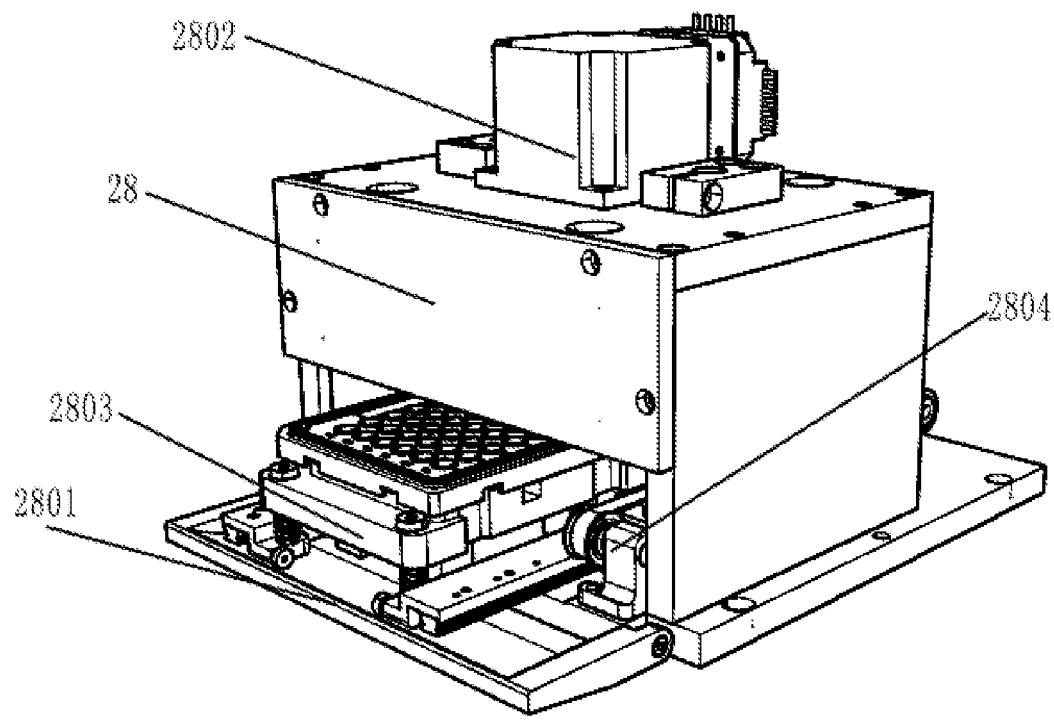
FIG. 12 is a schematic structural diagram of the heat sealing shell of the present disclosure.

As shown in FIG. 1, FIG. 10, and FIG. 12, the genetic testing device further includes heat sealing shell 28 and translation component H2804; the heat sealer 2802 and the translation component H2804 are arranged in the heat sealing shell 28; the heat sealing shell 28 is provided with a third switch door assembly 2801; the translation component H2804 is configured to make a sealing plate and a PCR plate move to a lower end of a heating plate of the heat sealer 2802; a moving function end of the translation component H2804 is fixedly provided with mounting plate F2803, and the PCR plate and the sealing plate are arranged on the mounting plate F2803; the mounting plate F2803 is in pressing contact with the third switch door assembly 2801; and a rebound direction of the third switch door assembly 2801 is towards the heat sealer 2802.

As shown in FIG. 1, the genetic testing device further includes a waste chamber arranged in the second mounting chamber C6, and first switch door assembly D is provided between the first mounting chamber C3 and the waste chamber.

As shown in FIG. 1, FIG. 2, FIG. 9, and FIG. 10, the first switch door assembly A7, the first switch door assembly B8, the first switch door assembly C9, the first switch door assembly D, the second switch door assembly A10, and the second switch door assembly B11 each include a door panel and an elastic member; two ends of the elastic member are fixedly connected to a mounting chamber and a first end of the door panel, respectively; and elastic members of the first switch door assembly A7, the first switch door assembly B8, the first switch door assembly C9, and the first switch door assembly D drive door panels to rotate upwards during deformation recovery, and elastic members of the second switch door assembly A10 and the second switch door assembly B11 drive door panels to rotate towards the second mounting chamber B5 during deformation recovery.

In this embodiment, the gripper A16 is controlled by the transfer assembly 12 to move downwards, such that the first switch door assembly A7, the first switch door assembly B8, the first switch door assembly C9, and the first switch door assembly D each are opened and thus a PCR plate is transferred between the mounting chambers of the upper part and the mounting chambers of the lower part; after the transfer is completed, the gripper A16 is controlled by the transfer assembly 12 to move upwards, the first switch door assembly A7, the first switch door assembly B8, the first switch door assembly C9, and the first switch door assembly D can be automatically closed under the action of elastic members, and the second switch door assembly A10 and the second switch door assembly B11 are opened by the material delivery module B, such that the PCR plate is transferred among the three mounting chambers of the lower part; and after the transfer is completed, the material delivery module B moves away from the second switch door assembly A10 or the second switch door assembly B11, and the second switch door assembly A10 and the second switch door assembly B11 can be automatically closed under the action of elastic members.

The translation component A1703, the translation component B2005, the translation component C1504, the translation component E24, the translation component F, the translation component G2501, the translation component H2804, and the translation component 130 each are any one selected from the group consisting of an air cylinder, an oil cylinder, a linear motor, a lead screw nut mechanism, and a gear wheel and gear rack.

The genetic testing device further includes a plurality of fixtures configured to fix the arrangement rack A1301, the arrangement rack B1302, the arrangement racks C1401, the arrangement racks D1402, and the arrangement rack E1403; each fixture includes an in-place sensor and an electromagnet; and when the in-place sensor detects that a corresponding arrangement rack is inserted into a specified place, the electromagnet adsorbs and fixes the corresponding arrangement rack.

In this embodiment, when the arrangement rack A1301 and the arrangement rack B1302 are inserted into the first mounting chamber A1 and the in-place sensor detects that the arrangement rack A1301 and the arrangement rack B1302 are inserted into specified places, the electromagnet is energized and the electromagnet adsorbs and fixes the arrangement rack A1301 and the arrangement rack B1302; and when the arrangement rack C1401, the arrangement rack D1402, and the arrangement rack E1403 are inserted into the first mounting chamber B2 and the in-place sensor detects that the arrangement rack C1401, the arrangement rack D1402, and the arrangement rack E1403 are inserted into specified places, the electromagnet is energized and the electromagnet adsorbs and fixes the arrangement rack C1401, the arrangement rack D1402, and the arrangement rack E1403.

A workflow of the genetic testing device of the present disclosure is as follows:

In the first mounting chamber A1, the arrangement rack A1301 and the arrangement rack B1302 are inserted, the sample injection module changes positions of the pipette assembly A 12-1-04 in the three directions of X, Y, and Z through the transfer assembly 12-1 to deliver an amplification reagent to a microwell of a PCR plate, then the gripper control member A16-1-01 controls the gripper A16-1 to grab the PCR plate with the amplification reagent, and the transfer assembly 12-1 makes the PCR plate move to a position directly above the first switch door assembly A7, and then the transfer assembly 12-1 controls the gripper A16-1 to move downwards such that the first switch door assembly A7 is opened, the PCR plate is placed on the bracket 22 of the material delivery module A and then transferred from the material delivery module A to the material delivery module B, and then the PCR plate is transferred by the material delivery module B to a position directly below the first switch door assembly B8.

In the first mounting chamber B2, the gripper A16-2 is transferred by the transfer assembly 12-4 to a position directly above the first switch door assembly B8, then the gripper A16-2 is controlled by the transfer assembly 12-4 to move downwards such that the first switch door assembly B8 is opened, and the PCR plate is grabbed and delivered to the first mounting chamber B2; the arrangement rack C1401, the arrangement rack D1402, the arrangement rack E1403, and the arrangement rack F1404 are inserted; the gripper C12-3-05 is transferred by the transfer assembly 12-3 to grab an 8-tube strip and place the 8-tube strip at the transposition 1411; the pipette assembly A12-2-04 configured to transfer a purification reagent is transferred by the transfer assembly 12-2 to transfer a corresponding purification reagent to the 8-tube strip, and then the gripper C12-3-05 is transferred by the transfer assembly 12-3 to grab a sample tube and transfer the sample tube to the opening-closing assembly 20 for uncapping; a gene sample to be tested in the sample tube is transferred to the 8-tube strip by the pipette assembly A12-3-04 configured to transfer a gene sample before purification, and then the 8-tube strip is transferred to the purification module 17 for a purification treatment; after the purification treatment is completed, a purified gene sample is transferred by the pipette assembly B29 to the PCR plate, then the PCR plate and the sealing plate are transferred by the gripper A16-2 to the mounting plate F2803, the translation component H2804 makes the sealing plate and the PCR plate move to the lower end of the heating plate of the heat sealer 2802, and the heat sealer 2802 hot-seals the sealing plate and the PCR plate together; and finally, the PCR plate obtained after the hot-sealing is transferred by the gripper A16-2 to a position directly above the first switch door assembly B8, then the gripper A16-2 is controlled by the transfer assembly 12-4 to move downwards such that the first switch door assembly B8 is opened, and the PCR plate is placed at the second end of the bracket 22 of the material delivery module B and then transferred from the material delivery module B to the material delivery module C, where the transferring function end of the material delivery module C is located directly below the first switch door assembly C9.

In the first mounting chamber C3, the gripper A is transferred by the transfer assembly 12-5 to a position directly above the first switch door assembly C9, then the gripper A is controlled by the transfer assembly 12-5 to move downwards such that the first switch door assembly C9 is opened, and the PCR plate is grabbed and transferred to the first mounting chamber C3; the PCR plate obtained after the hot-sealing is transferred to the heating base 1502, the translation component C1504 makes the heating base 1502 move such that the PCR plate is located directly below the hot cover assembly 1503, then the purified gene sample is subjected to amplification in a metal bath, and an amplified gene sample is subjected to optical detection and analysis by the optical detector 1501; and after the amplification detection is completed, the translation component C1504 makes the heating base 1502 move such that the PCR plate is removed and separated from the heating base 1502 by the transfer assembly 12-5 and gripper A, and a waste is discharged.

The technical solutions of the present disclosure are not limited to the above specific embodiments and all technical variations made according to the technical solutions of the present disclosure fall within the protection scope of the present disclosure.

What is claimed is:

1. A genetic testing device, comprising:
    a safety cabinet, wherein the safety cabinet is divided into an upper part and a lower part that are isolated from each other, and the upper part and the lower part of the safety cabinet each are divided into three mounting chambers that are isolated from one another;
    the three mounting chambers of the upper part are a first mounting chamber A, a first mounting chamber B, and a first mounting chamber C, and the three mounting chambers of the lower part are a second mounting chamber A, a second mounting chamber B, and a second mounting chamber C; and
    a first switch door assembly A is provided between the first mounting chamber A and the second mounting chamber A, a first switch door assembly B is provided between the first mounting chamber B and the second mounting chamber B, a first switch door assembly C is provided between the first mounting chamber C and the second mounting chamber C, a second switch door assembly A is provided between the second mounting chamber A and the second mounting chamber B, and a second switch door assembly B is provided between the second mounting chamber B and the second mounting chamber C;
    a gas flow control system configured to control gas pressure conditions of the first mounting chamber A, the first mounting chamber B, and the first mounting chamber C;
    a first treatment module configured to treat an amplification reagent and a polymerase chain reaction (PCR) plate; a second treatment module configured to treat a reagent, a tip, and a gene sample;
    a sample injection module configured to inject the amplification reagent into a microwell of the PCR plate;
    a purification treatment module configured to treat the gene sample;
    an amplification detection module for gene amplification and detection;
    a heat sealer configured to seal the PCR plate;
    a material delivery module A;
    a material delivery module B; and
    a material delivery module C, wherein the sample injection module and the first treatment module are arranged in the first mounting chamber A, the purification treatment module, the second treatment module, and the heat sealer are arranged in the first mounting chamber B, the amplification detection module is arranged in the first mounting chamber C, and the material delivery module A, the material delivery module B, and the material delivery module C are arranged in the second mounting chamber A, the second mounting chamber B, and the second mounting chamber C, respectively; the material delivery module A, the material delivery module B, and the material delivery module C are located below the sample injection module, the purification treatment module, and the amplification detection module, respectively; and
    during delivery, the sample injection module drives the PCR plate with the amplification reagent to pass through the first switch door assembly A and reach a transferring function end of the material delivery module A; when the material delivery module A delivers the PCR plate to the second switch door assembly A, the PCR plate is placed at a transferring function end of the material delivery module B; when the material delivery module B delivers the PCR plate to the first switch door assembly B, the PCR plate enters the first mounting chamber B through the purification treatment module, and a purified gene sample is added to the PCR plate; the PCR plate is hot-sealed by the heat sealer; the PCR plate with the gene sample is placed at the transferring function end of the material delivery module B through the purification treatment module and the first switch door assembly B; when the material delivery module B delivers the PCR plate to the second switch door assembly B, the PCR plate is placed at a transferring function end of the material delivery module C; and when the material delivery module C delivers the PCR plate to the first switch door assembly C, the PCR plate enters the first mounting chamber C through the purification treatment module, and the gene sample in the PCR plate is subjected to genetic testing by the amplification detection module;
    the sample injection module, the purification treatment module, and the amplification detection module each comprise a transfer assembly, a gripper A configured to transfer the PCR plate, and a gripper control member A configured to control an open or close of the gripper A, and the sample injection module and the purification treatment module each further comprise a pipette assembly A configured to transfer a liquid;
    the transfer assembly comprises:
    an X-direction moving component for X-direction movement, wherein the X-direction moving component comprises a motor A, a driving pulley A, a driven pulley A, a drive belt A, and a mounting plate A, the mounting plate A is fixedly connected to the drive belt A, a rotating shaft of the motor A is fixedly connected to a rotation center of the driving pulley A, and the driving pulley A and the driven pulley A are in a transmission connection through the drive belt A;
    a Y-direction moving component for Y-direction movement, wherein the Y-direction moving component comprises a motor B, a driving pulley B, a driven pulley B, a drive belt B, and a mounting plate B, the mounting plate B is fixedly connected to the drive belt B, a rotating shaft of the motor B is fixedly connected to a rotation center of the driving pulley B, and the driving pulley B and the driven pulley B are in a transmission connection through the drive belt B; and
    a Z-direction moving component for Z-direction movement, wherein the Z-direction moving component comprises a motor C, a lead screw nut mechanism A, and a mounting plate C, a rotating shaft of the motor C is fixedly connected to a lead screw A of the lead screw nut mechanism A, the mounting plate C is fixedly connected to a nut A of the lead screw nut mechanism A, and the gripper control member A and the pipette assembly A both are fixedly arranged on the mounting plate C;
    the X-direction moving components of the sample injection module and the amplification detection module are arranged on the mounting plate B, and the Z-direction moving components of the sample injection module and the amplification detection module are fixedly arranged on the mounting plate A; and
    the Y-direction moving component of the purification treatment module is arranged on the mounting plate A, and the Z-direction moving component of the purification treatment module is fixedly arranged on the mounting plate B.

2. The genetic testing device according to claim 1, wherein the first treatment module comprises
at least two arrangement racks A,
an arrangement rack B, and
a cooling module A configured to cool the amplification reagent; test tubes with amplification reagents are placed on the arrangement racks A, and a number of amplification reagents on one of the arrangement racks A is no less than a number of amplification reagents required for an experiment on a set of gene samples; the PCR plate is placed on the arrangement rack B; an opening is formed at a side of the first mounting chamber A; the arrangement racks A and the arrangement rack B both are placed in the first mounting chamber A in a drawer-type manner; and the cooling module A is arranged directly below the arrangement racks A.

3. The genetic testing device according to claim 2, wherein the second treatment module comprises
at least two arrangement racks C,
at least two arrangement racks D,
an arrangement rack E,
at least two temporary storage racks,
an arrangement rack F,
a vibrating member A configured to vibrate a magnetic bead solution,
a heating module configured to heat a lysis buffer, and
a cooling module B configured to cool a purified gene sample; purification reagents, 8-tube strips for a purification reaction, and replacement tips A are placed on the arrangement racks C, and a number of purification reagents, a number of 8-tube strips, and a number of replacement tips A on an arrangement rack C is no less than a number of purification reagents, a number of 8-tube strips, and a number of replacement tips A required for an experiment on a set of gene samples, respectively; sample tubes with gene samples are placed on the arrangement racks D, and a number of gene samples on one of the arrangement racks D is no less than a number of gene samples required for an experiment on a set of gene samples; a cleaning solution for eluting a gene sample is placed on the arrangement rack E; a replacement tip B and a sealing plate are placed on the arrangement rack F; a PCR plate without all purified gene samples filled is arranged on the temporary storage rack; the cooling module B is arranged directly below the temporary storage rack; an opening is formed at a side of the first mounting chamber B; and the arrangement racks C, the arrangement racks D, the arrangement rack E, and the arrangement rack F all are arranged in the first mounting chamber B in a drawer-type manner.

4. The genetic testing device according to claim 3, wherein the purification treatment module further comprises
at least one purification module,
a high-efficiency filter A, and
an induced draft fan A; the purification module comprises a heating oscillation chamber, a magnetic member, a vibrating member B, a translation component A, and a heating member; the heating oscillation chamber is provided with a reaction mounting rack, and the 8-tube strips for the purification reaction are placed on the reaction mounting rack; a heating function end of the heating member acts on the 8-tube strips, and the heating member is arranged at a vibrating function end of the vibrating member B; the translation component A is configured to drive the magnetic member to move and change an attraction of the magnetic member to magnetic beads in the 8-tube strips; and a gas outlet is formed at a side of the heating oscillation chamber, a gas inlet of the high-efficiency filter A communicates with the gas outlet of the heating oscillation chamber, and a gas inlet of the induced draft fan A communicates with a gas outlet of the high-efficiency filter A.

5. The genetic testing device according to claim 3, wherein the purification treatment module further comprises
an opening-closing assembly configured to open or close a tube cap of a sample tube; the opening-closing assembly comprises a lifting mechanism A, a gripper B, a gripper control member B configured to control an open or close of the gripper B, and a tube body-fixing member configured to fix a tube body of a sample tube; a lifting function end of the lifting mechanism A acts on the gripper control member B; and the tube body-fixing member is arranged below the gripper B.

6. The genetic testing device according to claim 5, wherein the tube body-fixing member comprises a fixing component A, a fixing component B, and a translation component B configured to control a distance between the fixing component A and the fixing component B; the fixing component B is arranged directly below the gripper B; a moving function end of the translation component B acts on the fixing component A; and opposite sides of the fixing component A and the fixing component B are arc surfaces, and an upper end of the arc surface of the fixing component A is provided with a snap ring configured to snap a sample tube.

7. The genetic testing device according to claim 1, wherein the amplification detection module further comprises
at least two metal bath modules,
at least two optical detectors, and
at least two translation components C; each metal bath module comprises a hot cover assembly and a heating base; the hot cover assembly is arranged at a detection port of an optical detector; and a moving function end of a translation component C acts on a heating base.

8. The genetic testing device according to claim 1, wherein the material delivery module A, the material delivery module B, and the material delivery module C each comprise
a bracket configured to receive the PCR plate; the material delivery module A and the material delivery module B each further comprise a translation component D, and the translation component D comprises a motor D, a slide rail, a driving pulley D, a driven pulley D, a drive belt D, and a mounting plate D; the mounting plate D is fixedly connected to the drive belt D, a rotating shaft of the motor D is fixedly connected to a rotation center of the driving pulley D, the driving pulley D and the driven pulley D are in a transmission connection through the drive belt D, the mounting plate D is slidably arranged in the slide rail, and the slide rail is fixedly arranged in a mounting chamber; the material delivery module A and the material delivery module C each comprise a lifting mechanism B configured to adjust a height of the bracket, and the lifting mechanism B is fixedly arranged on the mounting plate D; the material delivery module B further comprises a translation component E configured to drive the bracket to move, and the translation component E is fixedly arranged on the mounting plate D; two ends of the bracket in the material delivery module B are configured to receive a PCR plate with an amplification reagent and a PCR plate with a gene sample, respectively; and during delivery, at the second switch door assembly A, the material delivery module A delivers the PCR plate with the amplification reagent to the material delivery module B; and at the second switch door assembly B, the material delivery module B delivers the PCR plate with the gene sample to the material delivery module C, and a lifting function end of the lifting mechanism B of the material delivery module C is located directly below the first switch door assembly C.

9. The genetic testing device according to claim 1, wherein the gas flow control system comprises three gas flow members configured to control internal gas pressures of the first mounting chamber A, the first mounting chamber B, and the first mounting chamber C, respectively; each gas flow member comprises an induced draft fan B and an induced draft fan C; a gas outlet of the induced draft fan B communicates with a gas inlet of a mounting chamber, a gas inlet of the induced draft fan C communicates with a gas outlet of the mounting chamber, and a gas inlet of the induced draft fan B and the gas inlet of the induced draft fan C each are provided with a high-efficiency filter B; and the gas pressures of the first mounting chamber A, the first mounting chamber B, and the first mounting chamber C decrease sequentially, a gas pressure of the first mounting chamber A is greater than a gas pressure outside the safety cabinet, and a gas pressure of the first mounting chamber C is smaller than the gas pressure outside the safety cabinet.

10. The genetic testing device according to claim 3, wherein the second treatment module further comprises at least two translation components F and at least two induced draft components configured to draw an aerosol generated by a gene sample; a translation component F is provided to change a distance between a gas inlet of an induced draft component and the temporary storage rack; and during induced draft, the gas inlet of the induced draft component is located directly above a temporary storage rack.

11. The genetic testing device according to claim 1, wherein the genetic testing device further comprises
a solid-liquid waste discharge member arranged in the first mounting chamber B; the solid-liquid waste discharge member comprises a solid waste discharge chamber configured to discharge a solid waste, a liquid waste discharge chamber configured to discharge a liquid waste, a translation component G, and a cover plate; a moving function end of the translation component G acts on the cover plate; and the cover plate covers upper ends of the liquid waste discharge chamber and the solid waste discharge chamber.

12. The genetic testing device according to claim 3, wherein the arrangement racks D each are provided with a plurality of arrangement slots configured to receive sample tubes; a spring leaf is provided at a side of each of the arrangement slots, and a deformation recovery direction of the spring leaf is towards a central axis of the arrangement slots; and when a sample tube is placed in an arrangement slot, the spring leaf is in pressing contact with a side wall of the sample tube.

13. The genetic testing device according to claim 1, wherein the purification treatment module further comprises
two transfer assemblies, a gripper C configured to transfer a sample tube and an 8-tube strip, a gripper control member C configured to control an open or close of the gripper C, and two pipette assemblies A configured to transfer a liquid; the three pipette assemblies A of the purification treatment module are configured to transfer a purification reagent, a cleaning solution, and a gene sample, respectively; and the pipette assembly A configured to transfer a cleaning solution and the gripper control member A are arranged on a mounting plate C of a same transfer assembly, the pipette assembly A configured to transfer a gene sample and the gripper control member C are arranged on a mounting plate C of a same transfer assembly, and the pipette assembly A configured to transfer a purification reagent is arranged on a mounting plate C of the other transfer assembly.

14. The genetic testing device according to claim 1, wherein the genetic testing device further comprises
a heat sealing shell and a translation component H; the heat sealer and the translation component H are arranged in the heat sealing shell; the heat sealing shell is provided with a third switch door assembly; the translation component H is configured to drive a sealing plate and a PCR plate to move to a lower end of a heating plate of the heat sealer; a moving function end of the translation component H is fixedly provided with a mounting plate F, and the PCR plate and the sealing plate are arranged on the mounting plate F; the mounting plate F is in pressing contact with the third switch door assembly; and a rebound direction of the third switch door assembly is towards the heat sealer.

15. The genetic testing device according to claim 13, wherein the purification treatment module further comprises
a pipette assembly B for micropipetting, a translation component I, and
a liquid-receiving assembly configured to receive a liquid from the pipette assembly B; the liquid-receiving assembly comprises a liquid-receiving plate, a mounting shaft, a liquid-receiving rack, and a rotation-driving member configured to drive the liquid-receiving rack to rotate; a liquid-receiving groove is formed on the liquid-receiving plate; the mounting shaft and the translation component I are arranged on the same mounting plate C as the gripper control member A; a first end of the liquid-receiving rack is rotatably arranged on the mounting shaft, and a second end of the liquid-receiving rack is fixedly connected to the liquid-receiving plate; and the translation component I is configured to change relative positions of the liquid-receiving plate and the pipette assembly B in a dropping direction of a pipette assembly tip.

16. The genetic testing device according to claim 15, wherein the rotation-driving member comprises
a recess,
a boss, and
a torsion spring; the recess is formed on the liquid-receiving rack, the boss is fixedly arranged on the pipette assembly B, and the boss is always in pressing contact with the liquid-receiving rack; a first end of the torsion spring is fixedly connected to the first end of the liquid-receiving rack, and a second end of the torsion spring is fixedly connected to the mounting shaft; and the torsion spring is always in an energy storage state.

17. The genetic testing device according to claim 3, wherein the genetic testing device further comprises
a plurality of fixtures configured to fix the arrangement rack A, the arrangement rack B, the arrangement racks C, the arrangement racks D, and the arrangement rack E; each fixture comprises an in-place sensor and an electromagnet; and when the in-place sensor detects that a corresponding arrangement rack is inserted into a specified place, the electromagnet adsorbs and fixes the corresponding arrangement rack.

18. The genetic testing device according to claim 6, wherein the arc surfaces of the fixing component A and the fixing component B each are fixedly provided with a high-friction soft pad.

19. The genetic testing device according to claim 1, wherein the genetic testing device further comprises
   a waste chamber arranged in the second mounting chamber C, and a first switch door assembly D is provided between the first mounting chamber C and the waste chamber.

20. The genetic testing device according to claim 19, wherein the first switch door assembly A, the first switch door assembly B, the first switch door assembly C, the first switch door assembly D, the second switch door assembly A, and the second switch door assembly B each comprise a door panel and an elastic member; two ends of the elastic member are fixedly connected to a mounting chamber and a first end of the door panel, respectively; and elastic members of the first switch door assembly A, the first switch door assembly B, the first switch door assembly C, and the first switch door assembly D drive the door panels to rotate upwards during deformation recovery, and elastic members of the second switch door assembly A and the second switch door assembly B drive the door panels to rotate towards the second mounting chamber B during deformation recovery.

* * * * *